US012616385B2

(12) United States Patent
Takano et al.

(10) Patent No.: US 12,616,385 B2
(45) Date of Patent: May 5, 2026

(54) FLUID CIRCUIT AND BLOOD PRESSURE MEASUREMENT DEVICE

(71) Applicant: OMRON HEALTHCARE Co., Ltd., Kyoto (JP)

(72) Inventors: Yuki Takano, Kyoto (JP); Yoshihide Tokko, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 753 days.

(21) Appl. No.: 17/930,937

(22) Filed: Sep. 9, 2022

(65) Prior Publication Data

US 2023/0050831 A1     Feb. 16, 2023

Related U.S. Application Data

(63) Continuation of application No. PCT/JP2021/005505, filed on Feb. 15, 2021.

(30) Foreign Application Priority Data

Mar. 16, 2020    (JP) ................................. 2020-045403

(51) Int. Cl.
    *A61B 5/022*        (2006.01)
    *G05D 16/00*        (2006.01)
    *G05D 16/20*        (2006.01)
(52) U.S. Cl.
    CPC ....... *A61B 5/02233* (2013.01); *G05D 16/028* (2019.01); *G05D 16/208* (2013.01)
(58) Field of Classification Search
    CPC ..... A61B 5/021; A61B 5/02141; A61B 5/022; A61B 5/02225; A61B 5/02233; A61B 5/0235; A61B 5/025

USPC ........................ 600/490–492, 495, 498, 499
See application file for complete search history.

(56) References Cited

U.S. PATENT DOCUMENTS

| | | | | |
|---|---|---|---|---|
| 5,099,851 A | * | 3/1992 | Hata ................... | A61B 5/02208 |
| | | | | 600/490 |
| 2010/0324430 A1 | * | 12/2010 | Inoue ................. | A61B 5/02141 |
| | | | | 600/493 |
| 2019/0357782 A1 | * | 11/2019 | Tawara .............. | A61B 5/02141 |

FOREIGN PATENT DOCUMENTS

| | | |
|---|---|---|
| JP | 2008-5925 A | 1/2008 |
| JP | 2009-022477 A | 2/2009 |
| JP | 2009-284965 A | 12/2009 |
| JP | 2017-6488 A | 1/2017 |
| JP | 2018-130400 A | 8/2018 |

OTHER PUBLICATIONS

International Preliminary Report on Patentability for International Application No. PCT/JP2021/005505, Dated Sep. 20, 2022.

(Continued)

*Primary Examiner* — Puya Agahi
(74) *Attorney, Agent, or Firm* — Colson Law Group, PLLC

(57)                    ABSTRACT

A fluid circuit of a blood pressure measurement device includes a first cuff connected to a secondary side of a pump that supplies a fluid to a secondary side, a second cuff connected to a secondary side of the first cuff, a first valve provided between the first cuff and the second cuff, the first valve that closes when a differential pressure between the first cuff and the second cuff reaches a predetermined differential pressure, and a fluid resistor provided between the first valve and the second cuff.

5 Claims, 18 Drawing Sheets

(56)  References Cited

OTHER PUBLICATIONS

International Search Report for International Application No. PCT/
JP2021/005505, dated Apr. 13, 2021.

* cited by examiner

[FIG. 5]
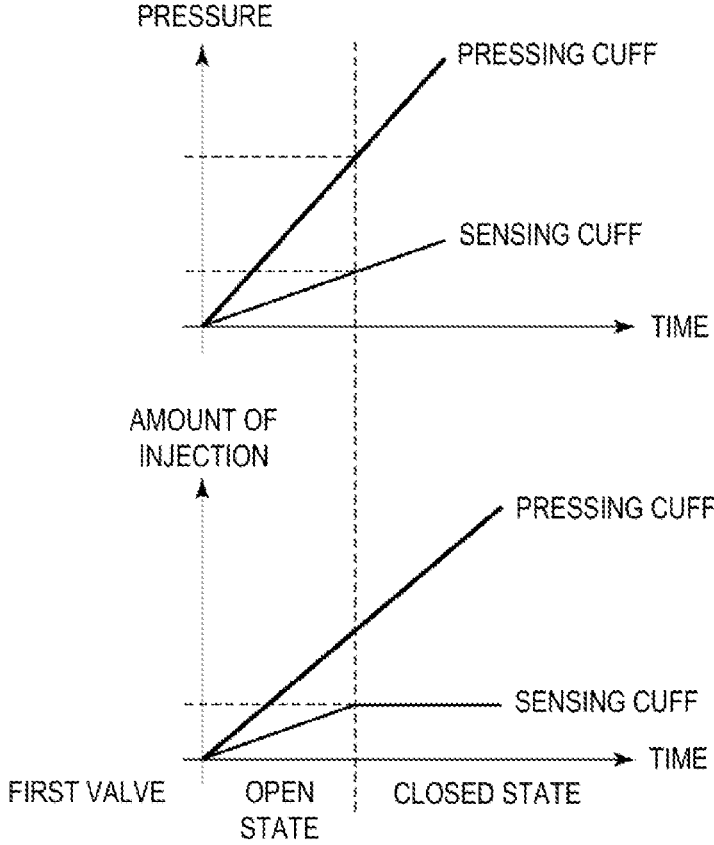
[FIG. 6]
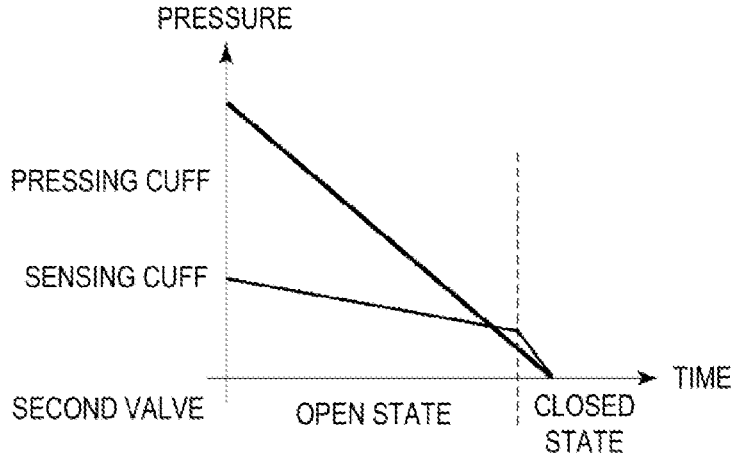

[FIG. 7]
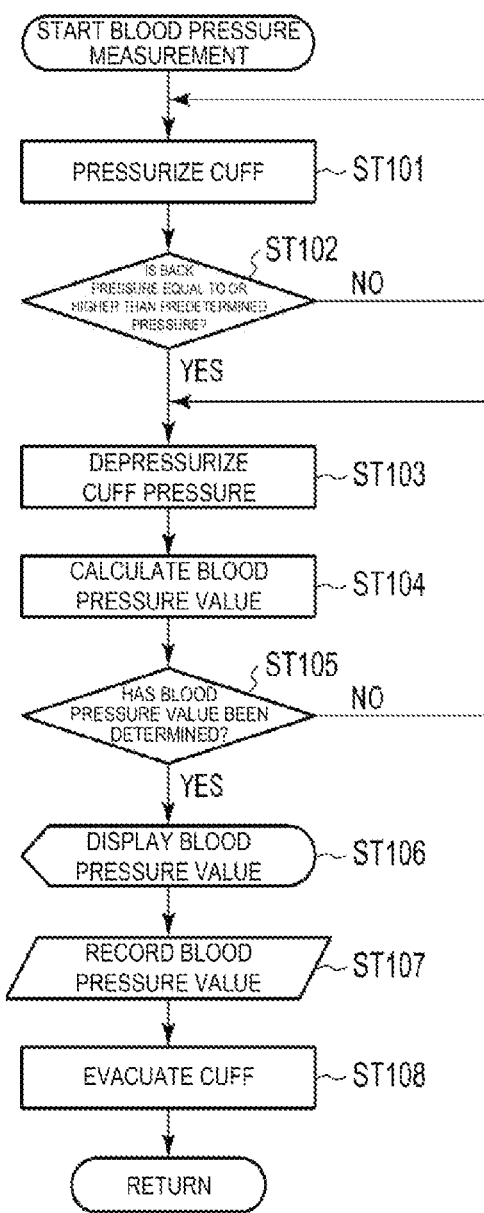

[FIG. 12]

FLUID CIRCUIT AND BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2021/005505, filed Feb. 15, 2021, which application claims priority to Japanese Patent Application No. 2020-045403, filed Mar. 16, 2020, which applications are incorporated herein by reference in their entireties.

TECHNICAL FIELD

The present invention relates to a fluid circuit and a blood pressure measurement device used for blood pressure measurement.

BACKGROUND ART

In recent years, blood pressure measurement devices used for measuring a blood pressure are being used as means to check health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, there is known a technique that the blood pressure measurement device includes a sensing cuff for measuring a blood pressure and a plurality of cuffs including a pressing cuff that presses the sensing cuff against a living body. The blood pressure measurement device includes a pump and supplies a fluid, for example, air to the cuff by the pump to inflate the cuff.

For example, JP 2009-22477 A discloses a technique of the blood pressure measurement device that disposes an orifice as a fluid resistor between a pressing cuff and a sensing cuff and includes a fluid circuit that reduces an amount of air injection. In such a blood pressure measurement device, a flow rate changes in proportion to a pressure difference between the pressing cuff on a primary side of the orifice and the sensing cuff on a secondary side of the orifice. Citation List—Patent Literature: Japanese Patent Application No.: JP 2009-22477 A.

SUMMARY OF INVENTION

Technical Problem

In the blood pressure measurement device described above, the flow rate of air supplied from a pump changes in proportion to the pressure difference between the pressing cuff on the primary side of the orifice and the sensing cuff on the secondary side of the orifice. Therefore, a change in pressurizing time of a living body during blood pressure measurement changes an amount of air inflow to the sensing cuff, causing an error in the amount of air injection to the sensing cuff.

Similarly, in a configuration including three or more cuffs, providing a fluid resistor, such as an orifice, between the cuff on the primary side and the cuff on the secondary side changes the amount of air inflow to the cuff on the secondary side.

In addition, the pressurization time of the living body during blood pressure measurement changes depending on, for example, a thickness of a measurement site of a subject, a state of winding of an arm band, and a pump property. Further, the amount of air injection supplied to the sensing cuff needs to be smaller than an amount of intake air supplied to the pressing cuff. Therefore, as the orifice provided between the pressing cuff and the sensing cuff, an orifice having a large fluid resistance needs to be used. Such an orifice requires a fine pinhole and requires expensive and highly accurate processing technique.

Thus, an object of the present invention is to provide a fluid circuit and a blood pressure measurement device that allow controlling an amount of air injection to a cuff to be constant.

Solution to Problem

According to an aspect, there is provided a fluid circuit that includes a first cuff, a second cuff, a first valve, and a fluid resistor. The first cuff is connected to a secondary side of a pump that supplies a fluid to a secondary side. The second cuff is connected to a secondary side of the first cuff. The first valve is provided between the first cuff and the second cuff. The first valve closes when a differential pressure between the first cuff and the second cuff reaches a predetermined differential pressure. The fluid resistor is provided on a secondary side of the first valve between the first valve and the second cuff.

Here, the fluid includes a liquid and air. The cuff includes a bag-like structure that is wound around, for example, an upper arm and a wrist of a living body when a blood pressure is measured and inflates by supply of a fluid. When the fluid is air, the bag-like structure is an air bag inflated by, for example, air.

According to this aspect, the fluid supplied to the secondary side by the pump is supplied to the first cuff, passes through the fluid resistor, and is supplied to the second cuff, and thus a flow rate of air supplied to the second cuff is smaller than a flow rate of air supplied to the first cuff. Therefore, a pressure of the first cuff is larger than a pressure of the second cuff. Further, when the differential pressure between the first cuff and the second cuff reaches the predetermined differential pressure, the first valve closes, and thus the supply of the fluid to the second cuff stops. Thus, the fluid circuit can make the amount of injection of fluid to the second cuff constant. Further, setting the first valve so as to close by the differential pressure between the first cuff and the second cuff when the second cuff reaches a desired pressure allows supplying the fluid by the supply amount where the pressure of the second cuff reaches the desired pressure to the second cuff.

In the fluid circuit according to the one aspect described above, there is provided a fluid circuit that includes a second valve. The second valve is provided in parallel with the first valve and the fluid resistor. The second valve opens when a pressure of the first cuff is lower than a pressure of the second cuff.

According to this aspect, in the fluid circuit, in a case where the pressure of the first cuff decreases due to, for example, exhaust of the fluids of the first cuff and the second cuff, when the pressure of the first cuff becomes lower than the pressure of the second cuff, the second valve opens. Thus, when the pressure of first cuff is higher than the pressure of the second cuff, the fluid of the first cuff is preferentially exhausted, and the fluid of the second cuff is exhausted through the fluid resistor. Additionally, when the pressure of the first cuff becomes lower than the pressure of the second cuff, the second valve opens and an exhaust rate of the fluid of the second cuff increases.

According to an aspect, there is provided a blood pressure measurement device that includes a pump, the fluid circuit, an on-off valve, a pressure sensor, and a control unit. The pump supplies a fluid to a secondary side. The fluid circuit is according to the one aspect described above. The on-off valve is provided between the pump and the first cuff. The on-off valve opens and closes a flow path to an atmosphere. The pressure sensor is connected to the second cuff. The control unit controls the pump and the on-off valve based on a pressure detected by the pressure sensor.

According to this aspect, the blood pressure measurement device can drive the pump based on the pressure of the second cuff, and thus the fluid can be supplied to the second cuff until at least the second cuff reaches a preferred pressure. Further, when the blood pressure measurement device exhausts the fluids of the first cuff and the second cuff, the fluids can be exhausted from the first cuff and the second cuff by controlling and opening the on-off valve by the control unit.

In the blood pressure measurement device according to the one aspect described above, there can be provided a blood pressure measurement device that includes a device body. The device body houses the pump, the on-off valve, the pressure sensor, and the control unit. The first valve and the fluid resistor are integrally provided with the first cuff.

According to this aspect, in the blood pressure measurement device, the device body houses the control unit, the pump controlled by the control unit, the on-off valve, and the pressure sensor. The first valve and the fluid resistor that are used for fluid control of the fluid circuit and not electrically connected to the control unit are integrally provided with the first cuff, and the device body does not house the first valve or the fluid resistor. Thus, the device body of the blood pressure measurement device can be miniaturized.

According to an aspect, there is provided a fluid circuit that includes a first cuff, a second cuff, a switching valve, and a fluid resistor. The first cuff is connected to a secondary side of a pump that supplies a fluid to a secondary side. The second cuff is provided to branch between the pump and the first cuff. The switching valve branches between the pump and the first cuff and is provided on a primary side of the second cuff. The switching valve is closed when a differential pressure between the first cuff and the second cuff reaches a predetermined differential pressure. The fluid resistor is provided between the switching valve and the second cuff.

According to this aspect, the fluid supplied to the secondary side by the pump is supplied to the first cuff and is supplied to the second cuff through the fluid resistor when the switching valve opens. Accordingly, the flow rate supplied to the second cuff is smaller than the flow rate of the air supplied to the first cuff. Therefore, a pressure of the first cuff is larger than a pressure of the second cuff. Further, when the differential pressure between the first cuff and the second cuff reaches the predetermined differential pressure, the switching valve is closed, and thus the supply of the fluid to the second cuff stops. Thus, in the fluid circuit, closing the switching valve makes an amount of supply of the fluid to the second cuff constant.

In the fluid circuit according to the one aspect described above, there can be provided a fluid circuit that includes a second valve. The second valve is provided in parallel with the fluid resistor. The second valve opens when a pressure of the first cuff is lower than a pressure of the second cuff.

According to this aspect, in the fluid circuit, in a case where the pressure of the first cuff decreases due to, for example, exhaust of the fluids of the first cuff and the second cuff, when the pressure of the first cuff becomes lower than the pressure of the second cuff, the second valve opens. Additionally, when the pressure of first cuff is higher than the pressure of the second cuff, the fluid of the first cuff is preferentially exhausted, and the fluid of the second cuff is exhausted through the fluid resistor. Additionally, when the pressure of the first cuff becomes lower than the pressure of the second cuff, the second valve opens and an exhaust rate of the fluid of the second cuff increases.

According to an aspect, there is provided a blood pressure measurement device that includes a pump, the fluid circuit, an on-off valve, a pressure sensor, and a control unit. The pump supplies a fluid to a secondary side. The fluid circuit is according to the one aspect described above. The on-off valve is provided among the pump, the first cuff, and the switching valve. The on-off valve opens and closes a flow path to an atmosphere. The pressure sensor is connected to the second cuff. The control unit controls the pump, the switching valve, and the on-off valve based on a pressure detected by the pressure sensor.

According to this aspect, the blood pressure measurement device can drive the pump based on the pressure of the second cuff, and thus the fluid can be supplied to the second cuff until at least the second cuff reaches a preferred pressure. Further, when the blood pressure measurement device exhausts the fluids of the first cuff and the second cuff, the fluids can be exhausted from the first cuff and the second cuff by controlling and opening the on-off valve by the control unit.

In the blood pressure measurement device according to the one aspect described above, there is provided a blood pressure measurement device that includes a device body. The device body houses the pump, the on-off valve, the switching valve, the pressure sensor, and the control unit. The first valve and the fluid resistor are integrally provided with the first cuff.

According to this aspect, the device body houses the control unit, the pump controlled by the control unit, the on-off valve, and the pressure sensor. The first valve and the fluid resistor that are used for fluid control of the fluid circuit and not electrically connected to the control unit are integrally provided with the first cuff, and the device body does not house the first valve or the fluid resistor. Thus, the device body of the blood pressure measurement device can be miniaturized.

Advantageous Effects of Invention

The present invention can provide the fluid circuit and the blood pressure measurement device that allow controlling an amount of air injection to the cuff to be constant.

BRIEF DESCRIPTION OF DRAWINGS

Various embodiments are disclosed, by way of example only, with reference to the accompanying schematic drawings in which corresponding reference symbols indicate corresponding parts, in which:

FIG. 5 is an explanatory view illustrating an example of a change in pressure and a change in amount of injection in blood pressure measurement by the blood pressure measurement device;

FIG. 6 is an explanatory view illustrating an example of a change in pressure during exhaust after blood pressure measurement by the blood pressure measurement device;

FIG. 7 is a flowchart depicting an example of usage of the blood pressure measurement device;

DESCRIPTION OF EMBODIMENTS

First Embodiment

An example of a blood pressure measurement device 1 according to the first embodiment of the present invention will be described below with reference to FIG. 1 to FIG. 7.

Figure 1:
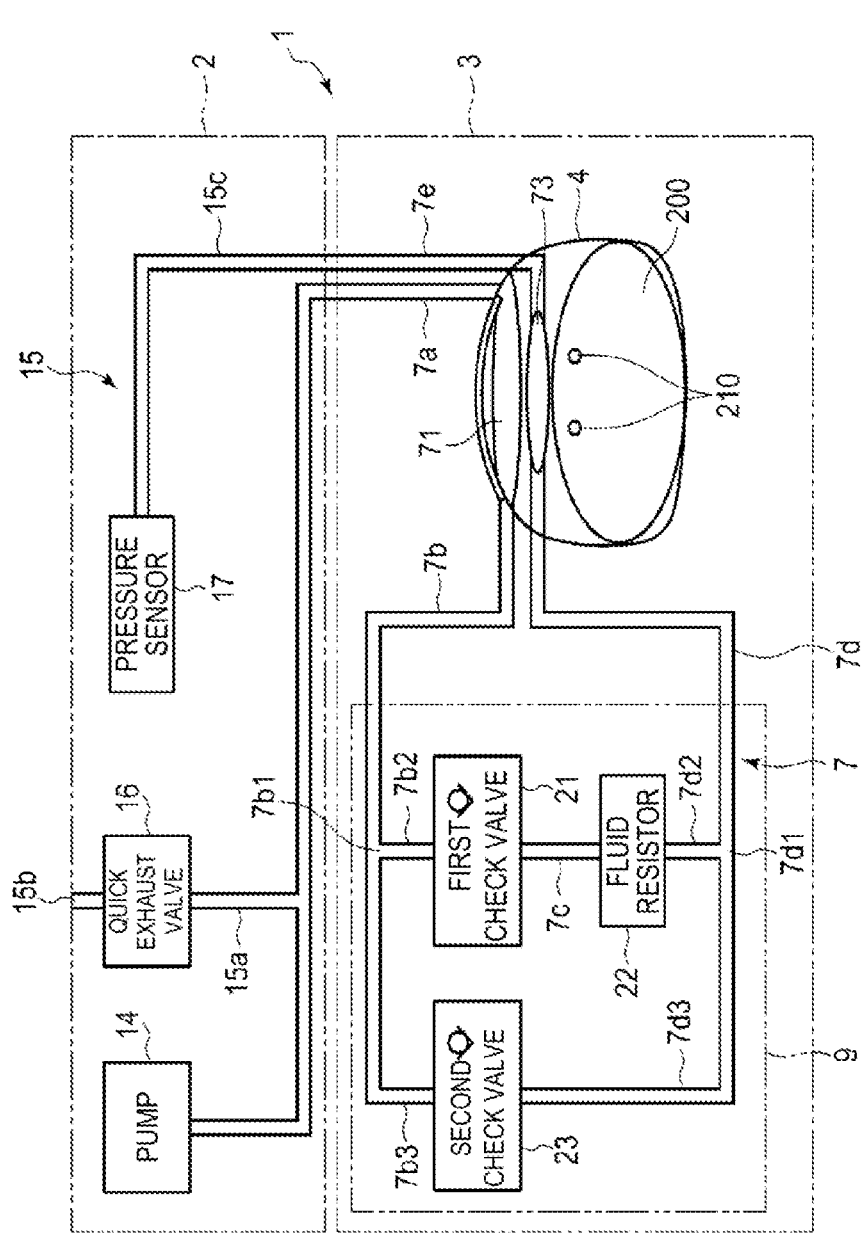
FIG. 1 is an explanatory view schematically illustrating a configuration of a blood pressure measurement device according to a first embodiment of the present invention.
Figure 2:
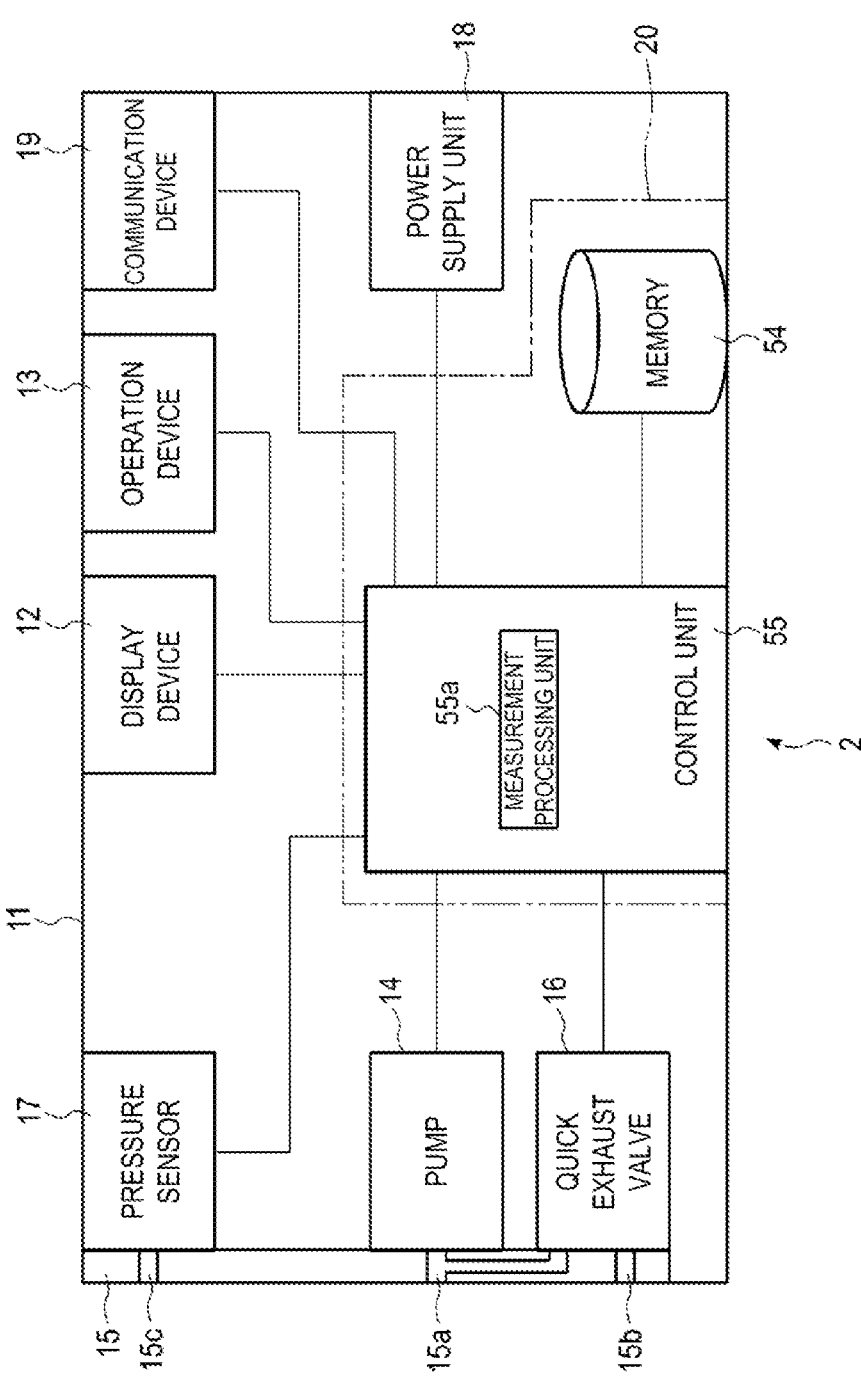
FIG. 2 is a block diagram schematically illustrating a configuration of a device body of the blood pressure measurement device.
Figure 3:
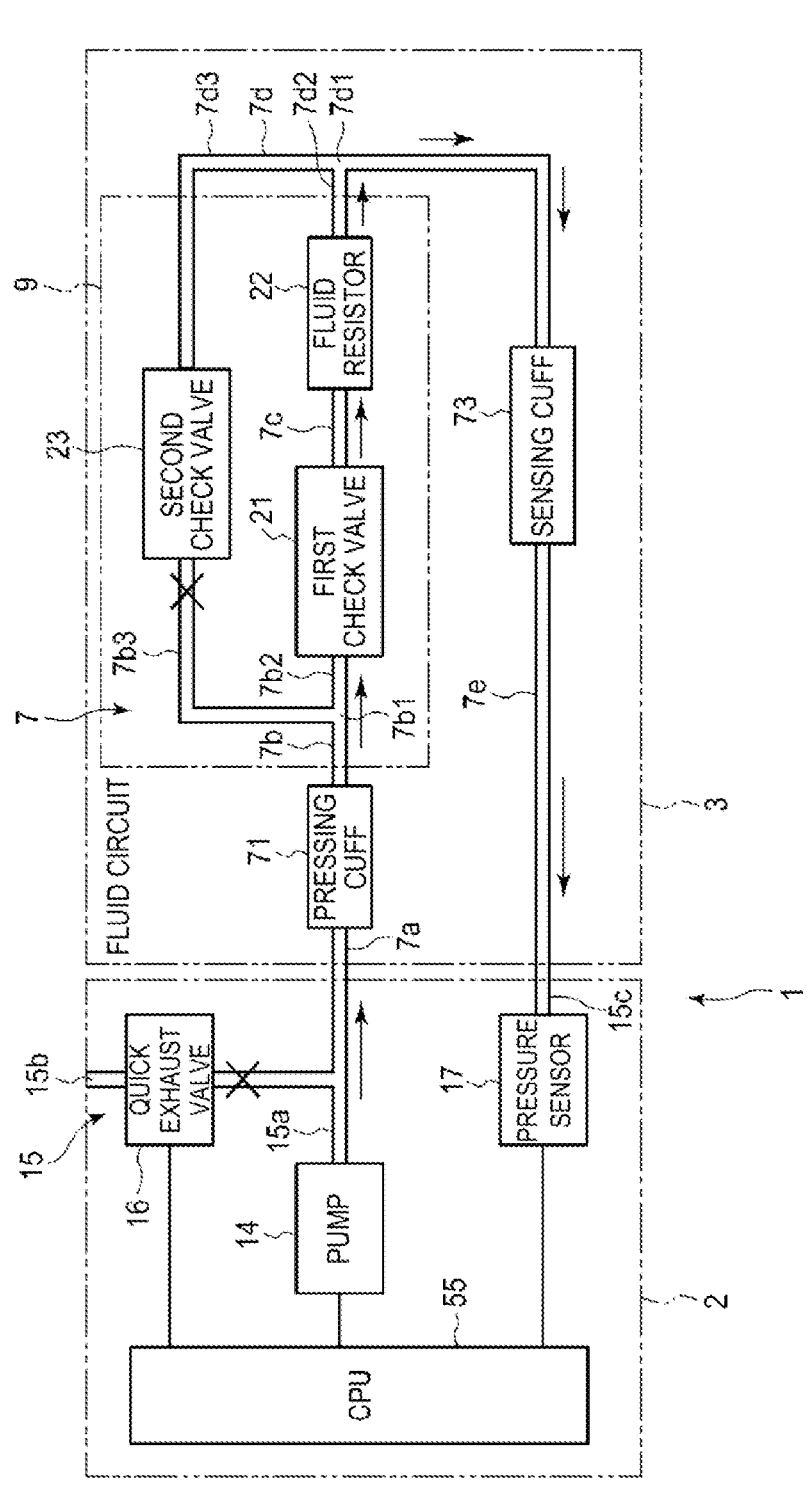
FIG. 3 is a block diagram illustrating the configuration of the blood pressure measurement device and illustrating an example of usage of the blood pressure measurement device.
Figure 4:
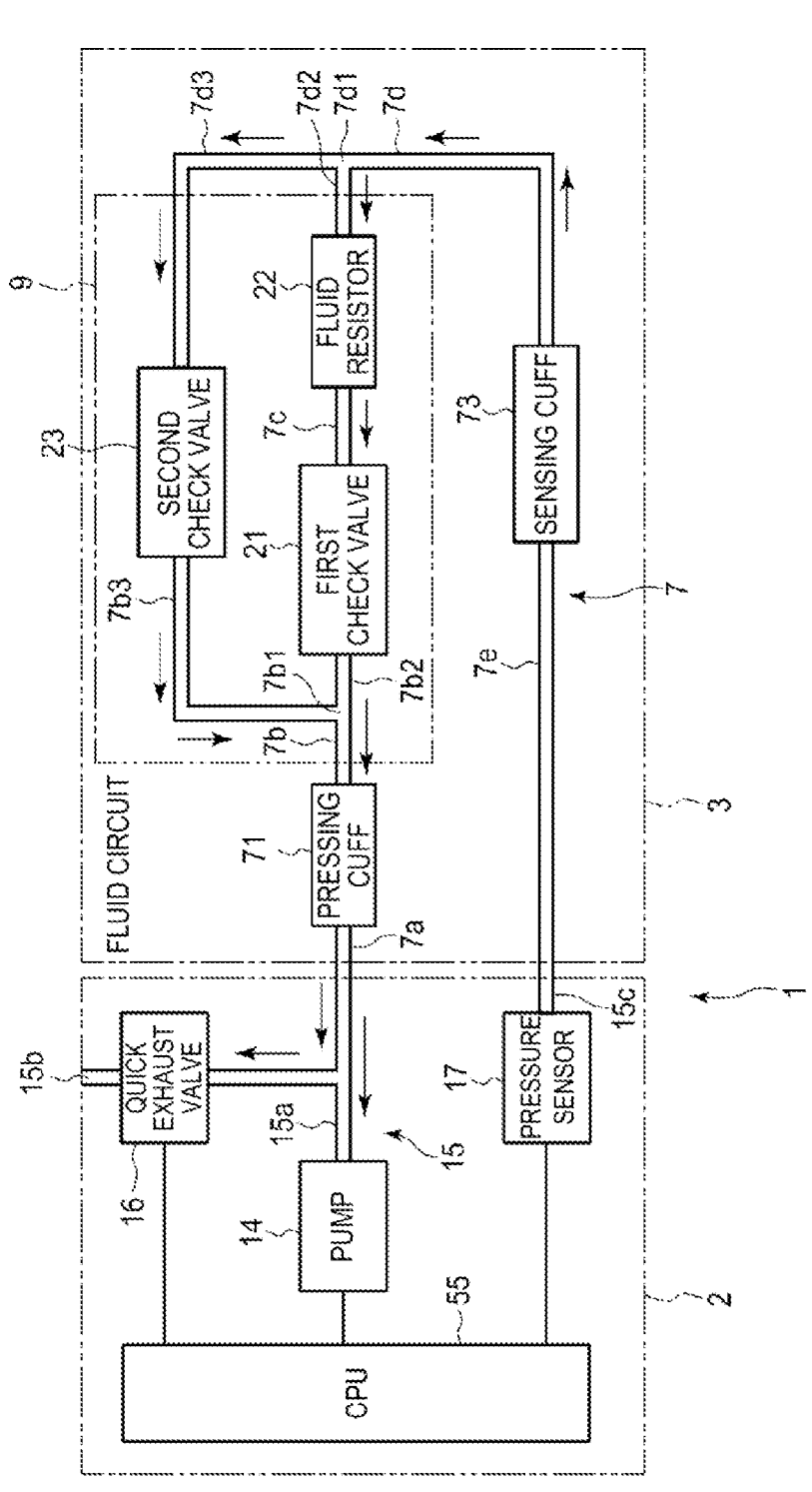
FIG. 4 is a block diagram illustrating the configuration of the blood pressure measurement device and illustrating an example of usage of the blood pressure measurement device.

FIG. 1 is an explanatory view schematically illustrating a configuration of the blood pressure measurement device 1 according to the first embodiment of the present invention. FIG. 2 is a block diagram schematically illustrating a configuration of a device body 2 of the blood pressure measurement device 1. FIG. 3 is a block diagram illustrating the configuration of the blood pressure measurement device 1 and illustrating an example of a flow of a fluid supplied to each of cuffs 71 and 73 in blood pressure measurement. FIG. 4 is a block diagram illustrating the configuration of the blood pressure measurement device 1 and illustrating an example of a flow of a fluid in exhaust of the fluid after blood pressure measurement. FIG. 5 is an explanatory view illustrating an example of a change in pressure and a change in amount of injection of each of the cuffs 71 and 73 in blood pressure measurement by the blood pressure measurement device 1. FIG. 6 is an explanatory view illustrating an example of a change in pressure of each of the cuffs 71 and 73 in exhaust of a fluid after blood pressure measurement by the blood pressure measurement device 1.

The blood pressure measurement device 1 is an electronic blood pressure measurement device attached to a living body. The blood pressure measurement device 1 is an electronic blood pressure measurement device that is attached to a living body 200, such as a wrist, and has an aspect of measuring a blood pressure from arteries 210 of the living body 200. As illustrated in FIG. 1, FIG. 3, and FIG. 4, the blood pressure measurement device 1 includes the device body 2 and a fluid circuit 3. For example, as illustrated in FIG. 1, the blood pressure measurement device 1 includes a fixture 4, such as a belt, that fixes at least the fluid circuit 3 to the living body 200. Note that FIG. 1 illustrates a wrist as the living body 200, but the living body 200 may be, for example, an upper arm.

As illustrated in FIG. 2, the device body 2 includes a case 11, a display device 12, an operation device 13, a pump 14, a flow path unit 15, an on-off valve 16, a pressure sensor 17, a power supply unit 18, a communication device 19, and a control substrate 20.

The case 11 houses, for example, the display device 12, the operation device 13, the pump 14, the flow path unit 15, the on-off valve 16, the pressure sensor 17, the power supply unit 18, the communication device 19, and the control substrate 20. Additionally, the case 11 exposes a portion of the display device 12 or is made of a transparent material such that a portion of the display device 12 can be visually recognized from the outside. Note that the case 11 may be configured to house a portion of the configuration of the fluid circuit 3.

The display device 12 is electrically connected to the control substrate 20. The display device 12 is, for example, a Liquid Crystal Display (LCD) or an Organic Electro Luminescence Display (OELD). The display device 12 displays various types of information including date and time and measurement results of, for example, blood pressure values, such as a systolic blood pressure and a diastolic blood pressure, and a heart rate in response to a control signal from the control substrate 20.

A user inputs an instruction with the operation device 13. For example, the operation device 13 is a sensor that includes a plurality of buttons and detects an operation of the button, for example, a pressure-sensitive or capacitive touch panel provided on, for example, the case 11 and the display device 12, and a microphone for receiving an instruction by sound. When operated by the user, the operation device 13 converts the instruction into an electrical signal and outputs the electrical signal to the control substrate 20.

The pump 14 is, for example, a piezoelectric pump. The pump 14 compresses a fluid and supplies the compressed fluid to the fluid circuit 3 through the flow path unit 15. The pump 14 is electrically connected to the control substrate 20. The pump 14 drives based on the control signal provided from the control substrate 20. Here, any gas or any liquid can be employed as the fluid. In the present embodiment, the fluid is air.

The flow path unit 15 connects the pump 14, the on-off valve 16, and the pressure sensor 17 to the fluid circuit 3. The flow path unit 15 is any of, for example, a tube, a pipe, a tank, and a hollow portion and a groove formed in the case 11, or a combination thereof. As a specific example, the flow path unit 15 forms a flow path from the pump 14 to a secondary side, and forms a flow path 15a that is formed by branching a portion of the flow path from the pump 14 to the secondary side. Thus, the flow path 15a connects to the on-off valve 16. The flow path unit 15 forms a flow path 15b that connects the on-off valve 16 to an atmosphere. The flow path unit 15 forms a flow path 15c that connects the pressure sensor 17 to the fluid circuit 3.

The on-off valve 16 is electrically connected to the control substrate 20. The on-off valve 16 is controlled by the control substrate 20. For example, the on-off valve 16 is opened and closed by control of the control substrate 20. The on-off valve 16 is connected to the atmosphere by the flow path unit 15 and is switched to an open state to connect the pump 14 and the fluid circuit 3 to the atmosphere.

The on-off valve 16 is an exhaust valve that opens the flow path on the secondary side of the pump 14 to the atmosphere. In addition, for example, the on-off valve 16 is, for example, a quick exhaust valve to set an opening degree of the on-off valve 16 or an opening area of the flow path unit 15 such that a fluid resistance becomes low as much as possible and allows quick exhaust. Note that each of the drawings illustrates the on-off valve 16 as the quick exhaust valve 16. The on-off valve 16 is switched to a closed state when air is supplied to the fluid circuit 3 during blood pressure measurement. In addition, when the fluid circuit 3 is exhausted, the on-off valve 16 is controlled by the control substrate 20 so as to be switched from the closed state to the open state. Further, the on-off valve 16 may be formed such that the opening degree is adjustable.

The pressure sensor 17 detects a pressure of the cuff disposed on the secondary side of the fluid circuit 3, and in the present embodiment, a pressure of a sensing cuff 73 described later of the fluid circuit 3. As a specific example, the pressure sensor 17 is fluidly connected to the sensing cuff 73 via the flow path unit 15, and detects the pressure inside the sensing cuff 73. The pressure sensor 17 is electrically connected to the control substrate 20. The pressure sensor 17 outputs an electrical signal corresponding to the detected pressure to the control substrate 20.

The power supply unit 18 is a power source. The power supply unit 18 is, for example, a secondary battery, such as a lithium ion battery. The power supply unit 18 is electrically connected to the control substrate 20. As a specific example, the power supply unit 18 supplies power to the control substrate 20. The power supply unit 18 supplies driving power to the respective configurations of the control substrate 20, the display device 12, the operation device 13, the pump 14, the on-off valve 16, the pressure sensor 17, and the communication device 19 via the control substrate 20.

The communication device 19 can transmit and receive information to and from an external device wirelessly or by wire. The communication device 19 transmits information, such as information controlled by the control substrate 20 and measured blood pressure values and pulse, to an external device, or receives, for example, a program for software update from an external device and transmits this to the control unit.

In the present embodiment, the external device is, for example, an external terminal, such as a smartphone, a tablet terminal, a personal computer, and a smart watch.

In the present embodiment, the communication device 19 and the external device may be directly connected, or may be connected over a network. The communication device 19 and the external device may be connected via a mobile communication network, such as 4G and 5G, and a wireless communication line, such as Wimax and Wi-Fi (registered trademark). Further, the communication device 19 and the external device may be connected by wireless communication means, such as Bluetooth (registered trademark), Near Field Communication (NFC), and infrared communication. Furthermore, the communication device 19 and the external device may be connected over a wired communication line, such as a Universal Serial Bus (USB) and a Local Area Network (LAN) connection with a cable. Thus, the communication device 19 may include a plurality of communication means, such as a wireless antenna and a micro-USB connector.

The control substrate 20 includes, for example, a substrate 51, a storage unit 54, and a control unit 55. The control substrate 20 is constituted by mounting the storage unit 54 and the control unit 55 on the substrate 51.

The substrate 51 is fixed to the case 11.

The storage unit 54 is a memory mounted on the substrate 51. The storage unit 54 includes, for example, a Random Access Memory (RAM) and a Read Only Memory (ROM). The storage unit 54 stores various types of data. For example, the storage unit 54 pre-stores, for example, program data for controlling the overall blood pressure measurement device 1, the pump 14, and the fluid circuit 3, settings data for setting various functions of the blood pressure measurement device 1, and calculation data for calculating a blood pressure value and a pulse from the pressure measured by the pressure sensor 17 to be changeable. The storage unit 54 stores information, such as a measured blood pressure value, a measured value of, for example, a pulse, and a pressure value measured by the pressure sensor 17. The storage unit 54 can store various types of data generated by a measurement processing unit 55a in the control unit 55.

The control unit 55 includes a single or a plurality of processors mounted on the substrate 51. For example, the processor is a Central Processing Unit (CPU). The control unit 55 controls the operation of the entire blood pressure measurement device 1 and the operations of the pump 14 and the fluid circuit 3 based on the programs stored in the storage unit 54 to perform a predetermined operation (function). In addition, in accordance with the read program, the control unit 55 performs, for example, predetermined operation, analysis, or process in the control unit 55.

The control unit 55 is electrically connected to and supplies power to the display device 12, the operation device 13, the pump 14, the on-off valve 16, and the pressure sensor 17. Additionally, the control unit 55 controls the operations of the display device 12, the pump 14, and the on-off valve 16, based on electrical signals output by the operation device 13 and the pressure sensor 17.

For example, the control unit 55 includes a main CPU that controls the operation of the overall blood pressure measurement device 1 and a sub-CPU that controls the operation of the fluid circuit 3. Note that, for example, the control unit 55 may be configured to perform all the controls of the blood pressure measurement device 1 in one CPU. For example, the main CPU obtains measurement results, such as blood pressure values, for example, the systolic blood pressure and the diastolic blood pressure, and the heart rate, from the electrical signals output by the pressure sensor 17, and outputs image signals corresponding to the measurement results to the display device 12.

For example, the sub-CPU drives the pump 14 and the on-off valve 16 to feed compressed air to the fluid circuit 3 when an instruction to measure the blood pressure is input from the operation device 13. In addition, the sub-CPU controls driving and stop of the pump 14 and opening and closing of the on-off valve 16 based on the electrical signal output by the pressure sensor 17. The sub-CPU controls the pump 14 and the on-off valve 16 to supply the compressed air to the fluid circuit 3 and selectively depressurize the fluid circuit 3.

Thus, the control unit 55 configures a portion of all of the respective functions performed by the control unit 55 in hardware by, for example, one or a plurality of integrated circuits. For example, the control unit 55 includes the measurement processing unit 55a. For example, the measurement processing unit 55a controls the pump 14 and the on-off valve 16 to supply air to the fluid circuit 3, and calculates the blood pressure by an oscillometric method based on the pressure of the sensing cuff 73 described later of the fluid circuit 3 detected by the pressure sensor 17.

The fluid circuit 3 includes a cuff structure 6, a tube group 7, and a fluid control unit 9. The fluid circuit 3 fluidly connects the cuff structure 6 and the fluid control unit 9 by the tube group 7.

Note that when air is supplied from the pump 14 to the fluid circuit 3, in the air flow, the pump 14 side (the device body 2 side) becomes the primary side and the fluid circuit 3 side becomes the secondary side. However, during exhaust, the on-off valve 16 side (the device body 2 side) becomes the secondary side and the fluid circuit 3 side becomes the primary side. However, in the description of the configuration of the fluid circuit 3, for convenience of explanation, the primary side and the secondary side are defined based on the flow direction of air when the air is supplied from the pump 14 to the cuff structure 6 and the tube group 7.

The cuff structure 6 includes a plurality of cuffs. Here, the cuff is wrapped around, for example, a wrist of a living body to measure a blood pressure and includes a single or multi-layer bag-like structures that are inflated by being supplied with a fluid. The bag-like structure is inflated by fluid. In the present embodiment, since the fluid is air, the bag-like structure is an air bag. The bag-like structure is formed, for example, by stacking and welding a pair of sheet members.

For example, the cuff structure 6 includes a first cuff 71 and the second cuff 73. The first cuff 71 is fluidly connected to the pump 14. The first cuff 71 is inflated by the air from the pump 14. The first cuff 71 is a pressing cuff that is inflated to press the second cuff 73 against the living body. Hereinafter, the first cuff 71 will be described as the pressing cuff 71. The pressing cuff 71 is formed by, for example, stacking a plurality of fluidly connected air bags in the pressing direction of the second cuff 73.

The second cuff 73 is provided on the secondary side of the first cuff 71. The second cuff 73 is inflated by air from the pump 14. The second cuff 73 is disposed in a region where the arteries 210 are present in the living body 200 when the blood pressure measurement device 1 is attached to the living body. The second cuff 73 is a sensing cuff for calculating the blood pressure in blood pressure measurement. Hereinafter, the second cuff 73 will be described as the sensing cuff 73. The sensing cuff 73 inflates to compress a region where the artery 210 is present in the living body 200.

The sensing cuff 73 is pressed to the wrist 200 side by the inflated pressing cuff 71. The sensing cuff 73 is formed by, for example, one air bag. The sensing cuff 73 is fluidly connected to the pressing cuff 71 via the fluid control unit 9. In the present embodiment, an example in which the sensing cuff 73 is fluidly connected to the secondary side of the pressing cuff 71 via the fluid control unit 9 will be described.

The tube group 7 is a collection of, for example, tubes or hollow portions provided between the sheet members constituting the air bag. The tube group 7, for example, may be integrally provided with the cuff structure 6, or may be separated from the cuff structure 6 and connected to the cuff structure 6.

The tube group 7 fluidly connects the pressing cuff 71, the sensing cuff 73, and the fluid control unit 9. The tube group 7 is connected to the flow path unit 15. In the present embodiment, an example of the tube group 7 in a configuration in which the fluid control unit 9 includes a first valve 21, a fluid resistor 22, and a second valve 23 will be described.

The tube group 7, for example, fluidly connects the pump 14, the on-off valve 16, and the pressing cuff 71 via the flow path unit 15. The tube group 7, for example, fluidly connects the pressure sensor 17 and the sensing cuff 73 via the flow path unit 15. Also, for example, the tube group 7 fluidly connects the first valve 21, the fluid resistor 22, and the sensing cuff 73 in series on the secondary side of the pressing cuff 71 and fluidly connects the first valve 21, the fluid resistor 22, and the second valve 23 in parallel.

Specifically, the tube group 7 includes a first tube 7a, a second tube 7b, a third tube 7c, a fourth tube 7d, and a fifth tube 7e. The first tube 7a is connected to the flow path 15a of the flow path unit 15 and the pressing cuff 71. The first tube 7a connects the pump 14, the on-off valve 16, and the pressing cuff 71 via the flow path unit 15.

The second tube 7b has a branch portion 7b1 in the middle portion from the primary side toward the secondary side, and is a branch pipe branched into two flow paths at the branch portion 7b1. The primary side of the second tube 7b is fluidly connected to the pressing cuff 71. One branched tube portion 7b2 on the secondary side of the second tube 7b is connected to the first valve 21. An other branched tube portion 7b3 on the secondary side of the second tube 7b is connected to the second valve 23.

The third tube 7c is connected to the first valve 21 and the fluid resistor 22. The fourth tube 7d is a joining tube having a joint portion 7d1 that joins two flow paths to one at the middle portion from the primary side toward the secondary side. One tube portion 7d2, which is on the primary side than the joint portion 7d1 of the fourth tube 7d, is connected to the fluid resistor 22. An other tube portion 7d3 on the primary side than the joint portion 7d1 of the fourth tube 7d is connected to the second valve 23. The secondary side of the fourth tube 7d is connected to the sensing cuff 73.

The fifth tube 7e is connected to the flow path 15c of the flow path unit 15 and the sensing cuff 73. The fifth tube 7e connects the pressure sensor 17 and the sensing cuff 73 via the flow path unit 15.

The fluid control unit 9 controls a flow rate of air to reduce a flow rate of air flowing from the primary side to the secondary side and regulates the flow of air at a predetermined amount of injection to control the amount of injection of the cuff on the secondary side to be constant. The fluid control unit 9 controls the pressure on the primary side and the pressure on the secondary side of the fluid control unit 9.

As a specific example, the fluid control unit 9 reduces the flow rate of air flowing from the pressing cuff 71 side to the sensing cuff 73 and stops supplying the air to the sensing cuff 73 at the predetermined amount of injection. Then, the fluid control unit 9 sets the amount of injection of air to the sensing cuff 73 as the predetermined amount of injection and controls the amount of injection of air supplied to the sensing cuff 73 to be constant and controls the pressures of the pressing cuff 71 and the sensing cuff 73. The fluid control unit 9 includes, for example, the first valve 21, the fluid resistor 22, and the second valve 23.

The first valve 21 closes when the pressure on the primary side is higher than the pressure on the secondary side by a predetermined pressure. Specifically, the first valve 21 closes when the pressure on the pressing cuff 71 side becomes higher than the pressure on the sensing cuff 73 side by equal to or more than the predetermined pressure. The first valve 21, for example, always opens, and closes when a differential pressure between the pressure of the pressing cuff 71 and the pressure of the sensing cuff 73 becomes a cracking pressure that is high by a predetermined pressure. The first valve 21 is, for example, a check valve. In each of the drawings, the first valve 21 is illustrated as the first check valve 21.

For example, the cracking pressure of the first valve 21 is set to a pressure preferred for blood pressure measurement using the pressing cuff 71 and the sensing cuff 73. As a specific example, the cracking pressure of the first valve 21 is set to 70 mm Hg such that the first valve 21 closes when the pressure of the pressing cuff 71 reaches 100 mm Hg and the pressure of the sensing cuff 73 reaches 30 mm Hg.

The fluid resistor 22 provides a resistance of the passing fluid, air in the present embodiment. The fluid resistor 22 has, for example, a flow path cross-sectional area smaller than flow path cross-sectional areas on the primary side and the secondary side of the fluid resistor 22, that is, flow path cross-sectional areas of the third tube 7*c* and the fourth tube 7*d*. The fluid resistor 22 is, for example, an orifice. The fluid resistor 22 partially reduces the flow path on the flow path on the primary side of the sensing cuff 73 to lower the amount of injection of air to the sensing cuff 73 than the amount of injection of air supplied to the pressing cuff 71. A resistance value of the fluid resistor 22 is set to a value in which the amounts of injection of air to the pressing cuff 71 and the sensing cuff 73 become preferred amounts of injection and the pressures of the pressing cuff 71 and the sensing cuff 73 become desired pressures. For example, as described above, the fluid resistor 22 is set to a resistance value at which the pressure of the sensing cuff 73 is 30 mm Hg when the pressure of the pressing cuff 71 is 100 mm Hg.

The second valve 23 opens when the pressure on the primary side is lower than the pressure on the secondary side. Specifically, the second valve 23 closes when the pressure on the pressing cuff 71 side is equal to or more than the pressure on the sensing cuff 73 side and opens when the pressure on the pressing cuff 71 side is lower than the pressure on the sensing cuff 73 side. The second valve 23 always closes when air is supplied to the pressing cuff 71 and the sensing cuff 73 during blood pressure measurement, for example. Additionally, the second valve 23 opens when the differential pressure between the pressure of the pressure of the pressing cuff 71 and the pressure of the sensing cuff 73 is eliminated during exhaust while the pressure of the pressing cuff 71 becomes a cracking pressure in which the pressure of the pressing cuff 71 falls below the pressure of the sensing cuff 73. The second valve 23 is, for example, a check valve. In each of the drawings, the second valve 23 is illustrated as the second check valve 23.

For example, a cracking pressure of the second valve 23 is set to a preferred pressure for exhaust of the pressing cuff 71 and the sensing cuff 73. As a specific example, the cracking pressure of the second valve 23 is set to 0 mm Hg such that the second valve 23 opens when the pressure of the pressing cuff 71 falls below the pressure of the sensing cuff 73.

Note that the second valve 23 is configured to prevent the air in the pressing cuff 71 from flowing toward the sensing cuff 73 side during exhaust, and open when the pressure on the primary side is lower than the pressure on the secondary side. However, when the air does not substantially flow from the pressing cuff 71 to the sensing cuff 73 in exhaust of the fluid circuit 3, the second valve 23 may be set to have the cracking pressure in which the second valve 23 opens when the pressure on the primary side is slightly higher than the pressure on the secondary side.

Next, an example of the change in pressures of the pressing cuff 71 and the sensing cuff 73 and the amount of injection of air when air is supplied to the fluid circuit 3 will be described with reference to FIG. 3 and FIG. 5. FIG. 3 indicates the air flow by the arrows and a flow path where each valve closes by X. FIG. 5 illustrates an example of an open state and a closed state of the first valve 21.

In the fluid circuit 3, the on-off valve 16 is closed by the measurement processing unit 55*a* in the control unit 55 during blood pressure measurement, and when the pump 14 starts driving, the air is first supplied to the pressing cuff 71. At this time, the first valve 21 opens. Since the air is supplied to the pressing cuff 71 first, the second valve 23 closes. Thus, the air supplied to the pressing cuff 71 is supplied to the sensing cuff 73 via the first valve 21 and the fluid resistor 22. At this time, since the air supplied to the sensing cuff 73 passes through the fluid resistor 22, as illustrated in FIG. 5, the amount of injection of air to the sensing cuff 73 is less than the amount of injection of air to the pressing cuff 71. Thus, the increases in pressure of the pressing cuff 71 and the sensing cuff 73 differ, a relationship in which the pressure of the pressing cuff 71 is higher than the pressure of the sensing cuff 73 is maintained, and the pressing cuff 71 and the sensing cuff 73 increase the pressures.

When the differential pressure between the pressing cuff 71 and the sensing cuff 73 reaches the cracking pressure of the first valve 21, the first valve 21 closes. When the first valve 21 is in the closed state, afterward, the air supplied by the pump 14 is supplied to only the pressing cuff 71. Thus, as illustrated in FIG. 5, after the first valve 21 closes, the amount of injection of air to the pressing cuff 71 increases, but the amount of injection of air to the sensing cuff 73 does not increase, and the amount of injection remains the amount of injection when the first valve 21 closes and is constant. Note that, since the sensing cuff 73 is pressed to the living body 200 by the inflated pressing cuff 71, the amount of injection of air to the sensing cuff 73 does not change, but the pressure of the sensing cuff 73 increases. Accordingly, during blood pressure measurement, the pressures of the pressing cuff 71 and the sensing cuff 73 increase up to the pressures preferred for blood pressure measurement.

Next, an example of the change in pressures of the pressing cuff 71 and the sensing cuff 73 when the air supplied to the fluid circuit 3 is exhausted will be described with reference to FIG. 4 and FIG. 6. FIG. 4 indicates the air flow by the arrows. Further, FIG. 6 illustrates an example of the open state and the closed state of the second valve 23.

In the fluid circuit 3, when the exhaust of the fluid circuit 3 starts after the blood pressure measurement, the pump 14 is stopped by the measurement processing unit 55a in the control unit 55 and the on-off valve 16 opens, and thus the on-off valve 16 side of the pressing cuff 71 is connected to the atmosphere. Thus, the air in the pressing cuff 71 flows toward the on-off valve 16 side, and the pressure of the pressing cuff 71 decreases. Note that at this time, the first valve 21 and the second valve 23 close.

As the exhaust of the pressing cuff 71 progresses, the pressure of the pressing cuff 71 decreases. Therefore, as illustrated in FIG. 6, a pressing force of the sensing cuff 73 by the pressing cuff 71 decreases, and the pressure of the sensing cuff 73 also decreases. When the exhaust of the pressing cuff 71 progresses and the differential pressure between the pressing cuff 71 and the sensing cuff 73 falls below the cracking pressure of the first valve 21, the first valve 21 opens. As a result, the air in the sensing cuff 73 flows toward the on-off valve 16 via the fluid resistor 22 and the pressing cuff 71. Note that an exhaust volume of air exhausted from the sensing cuff 73 is reduced by the fluid resistor 22 and is smaller than the exhaust volume of air in the pressing cuff 71.

Then, when the pressure of the pressing cuff 71 decreases and becomes lower than the pressure of the sensing cuff 73, as illustrated in FIG. 6, the second valve 23 switches from the closed state to the open state. When the second valve 23 opens, the flow path through the second valve 23 becomes a bypass path, and an exhaust speed of the sensing cuff 73 increases. Then, the exhaust of the pressing cuff 71 and the sensing cuff 73 proceeds, and the pressures of the pressing cuff 71 and the sensing cuff 73 become atmospheric pressures. In this way, in the exhaust of the fluid circuit 3, the pressing cuff 71 is preferentially and quickly exhausted than the sensing cuff 73. In the fluid circuit 3, when the pressure of the pressing cuff 71 falls below the pressure of the sensing cuff 73, the second valve 23 opens, and the pressing cuff 71 and the sensing cuff 73 are quickly exhausted. As such, the fluid circuit 3 is exhausted.

Next, an example of the control during blood pressure measurement using the blood pressure measurement device 1 configured in this manner will be described with reference to the flowchart depicted in FIG. 7.

First, with the blood pressure measurement device 1 attached to the living body 200, the user operates the operation device 13 to perform the instruction to start the blood pressure measurement. The operation device 13 outputs the electrical signal to the control unit 55 as the instruction to start the blood pressure measurement. When the control unit 55 receives the electrical signal from the operation device 13, the measurement processing unit 55a switches the on-off valve 16 to the closed state, starts driving the pump 14, and pressurizes the pressing cuff 71 and the sensing cuff 73 (step ST101). Then, the measurement processing unit 55a determines whether the pressure measured by the pressure sensor 17 is a predetermined pressure (step ST102). Here, the predetermined pressure is the pressure of the sensing cuff 73 at which the blood pressure can be measured by the sensing cuff 73 and is stored in the storage unit 54 in advance.

When the pressure of the sensing cuff 73 is not the predetermined pressure (NO in step ST102), the measurement processing unit 55a continues driving the pump 14. When the pressure of the sensing cuff 73 reaches the predetermined pressure (YES in step ST102), the measurement processing unit 55a stops the pump 14 and stops supplying air to the pressing cuff 71. Furthermore, the measurement processing unit 55a switches the on-off valve 16 to the open state and starts depressurizing the pressing cuff 71 (step ST103). At this time, the measurement processing unit 55a adjusts the degree of opening of the on-off valve 16 or repeatedly switches the opening/closing of the on-off valve 16, and thus the pressing cuff 71 is depressurized gently.

The measurement processing unit 55a calculates the blood pressure value from the pressure measured by the pressure sensor 17 (step ST104). Next, the measurement processing unit 55a determines whether the calculated value should be determined as the blood pressure value (step ST105). Note that a threshold value for whether the calculated value should be determined as the blood pressure value is stored in the storage unit 54 in advance. Also, the threshold value for determining the blood pressure value is appropriately set by, for example, the detected blood pressure value and the pressure of the sensing cuff 73. When the calculated value cannot be determined as the blood pressure value (NO in step ST105), the measurement processing unit 55a continues depressurizing the pressing cuff 71 (step ST103). In a case where the calculated value is determined as the blood pressure value (YES in step ST105), the measurement processing unit 55a displays the blood pressure value on the display device 12 (step ST106), and records (stores) the measured blood pressure value in the storage unit 54 (step ST107). The measurement processing unit 55a is then maximizes the degree of opening of the on-off valve 16 or sets the on-off valve 16 in the open state, and exhausts the pressing cuff and the sensing cuff 73 (step ST108). Then, the measurement processing unit 55a ends the blood pressure measurement and stands by for the next instruction to start blood pressure measurement. When the measurement processing unit 55a receives the instruction to start blood pressure measurement, returns the step again to step ST101, and starts the blood pressure measurement.

According to the blood pressure measurement device 1 configured in this manner, the fluid circuit 3 includes the fluid resistor 22 as the fluid control unit 9, which is disposed between the pressing cuff 71 and the sensing cuff 73, that reduces the flow rate of air to the first valve 21, which closes at the cracking pressure, and the secondary side. Thus, when air is supplied to the pressing cuff 71 and the sensing cuff 73 by the pump 14, the differential pressure occurs between the pressing cuff 71 and the sensing cuff 73. When the differential pressure becomes the cracking pressure of the first valve 21, the first valve 21 closes, and thus the fluid control unit 9 can supply air to the sensing cuff 73 by the predetermined amount of injection. This eliminates the need for the step of an injection process of air by the measurement processing unit 55a in the control unit 55 in blood pressure measurement, thus shortening the blood pressure measurement time. Therefore, an influence of artifact, such as body movement, is solved, and the blood pressure measurement device 1 improves in robustness in actual use.

The amount of injection of air and the pressure difference of the air between the pressing cuff 71 and the sensing cuff 73 can be set by the cracking pressure of the first valve 21 and the resistance value of the fluid resistor 22. Thus, the amount of injection of air to the sensing cuff 73 can be constant with the first valve 21 and the fluid resistor 22. That is, by controlling the flow rate of air supplied to the secondary side using the supplied fluid by the fluid control unit 9, the blood pressure measurement device 1 does not require a component that is electrically controlled by, for example, the control unit 55 other than the pump 14 or the on-off valve 16 to make the amount of injection to the sensing cuff 73 constant at the desired amount of injection. Thus, the blood pressure measurement device 1 can simplify the control in blood pressure measurement and reduce the power consumption. Furthermore, the first valve 21, the fluid resistor 22, or the second valve 23, which does not require electrical control, need not be disposed in the device body 2, and providing the fluid control unit 9 outside the device body 2 allows miniaturizing the device body 2.

Also, when the fluid resistor 22 is provided, when the air flows from the sensing cuff 73 to the atmosphere through the pressing cuff 71 during exhaust of the fluid circuit 3, the flow of air is inhibited, and the exhaust speed decreases. However, in the blood pressure measurement device 1, the second valve 23, which opens when the pressure of the pressing cuff 71 becomes lower than the pressure of the sensing cuff 73, is provided in parallel with the flow path passing through the first valve 21 and the fluid resistor 22. Thus, the air in the sensing cuff 73 is exhausted to the atmosphere via the pressing cuff 71 through the bypass path passing through the second valve 23, in addition to the flow path through the fluid resistor 22 and the first valve 21. Thus, the configuration including the fluid resistor 22 also allows preventing the reduction in exhaust speed of the sensing cuff 73. Additionally, the pressing cuff 71, which compresses the living body 200 more, is preferentially exhausted, and when the pressure of the pressing cuff 71 falls below that of the sensing cuff 73, an exhaust speed of the sensing cuff 73 increases. Thus, the blood pressure measurement device 1 can reduce a load on the living body due to the compression of the living body after the end of blood pressure measurement and the exhaust time of the sensing cuff 73 can be shortened.

As described above, according to the blood pressure measurement device 1 according to the first embodiment, the sensing cuff 73 is provided on the secondary side of the pressing cuff 71, and the first valve 21 and the fluid resistor 22 that close by the differential pressure between the pressing cuff 71 and the sensing cuff 73 are provided between the pressing cuff 71 and the sensing cuff 73. Thus, the blood pressure measurement device 1 allows controlling the amount of air injection to the sensing cuff 73 to be constant.

Second Embodiment

Figure 8:
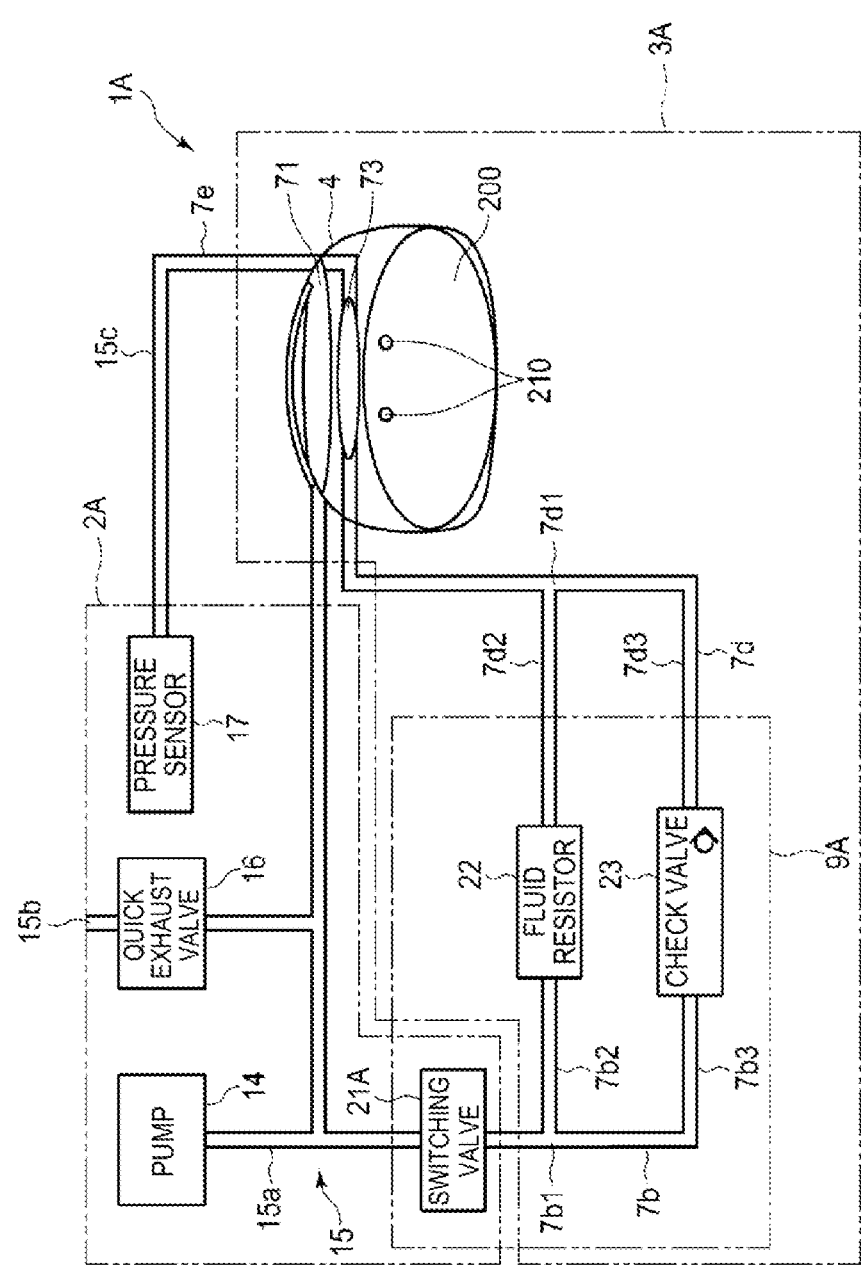
FIG. 8 is an explanatory view schematically illustrating a configuration of a blood pressure measurement device according to a second embodiment of the present invention.
Figure 9:
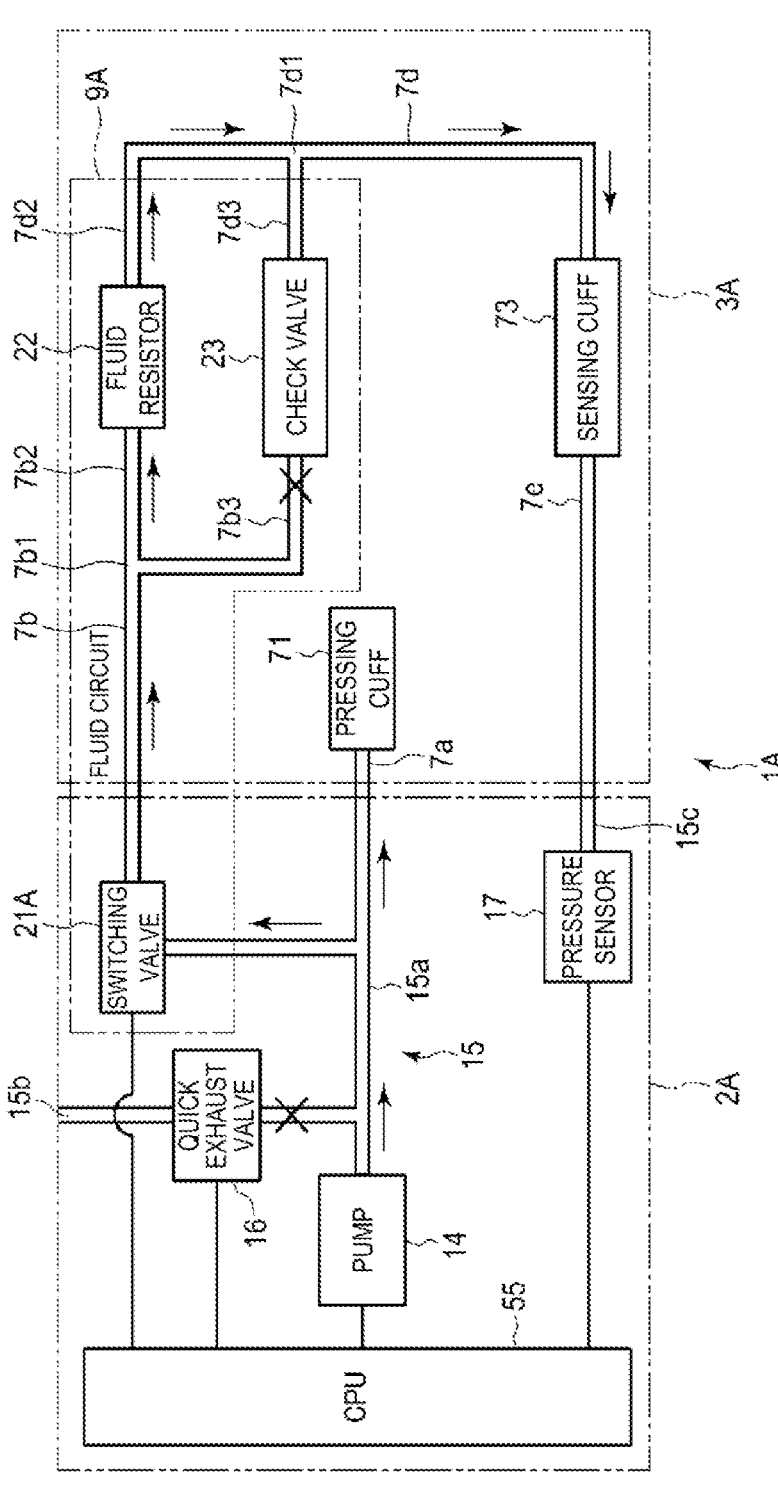
FIG. 9 is a block diagram illustrating the configuration of the blood pressure measurement device and illustrating an example of usage of the blood pressure measurement device.
Figure 10:
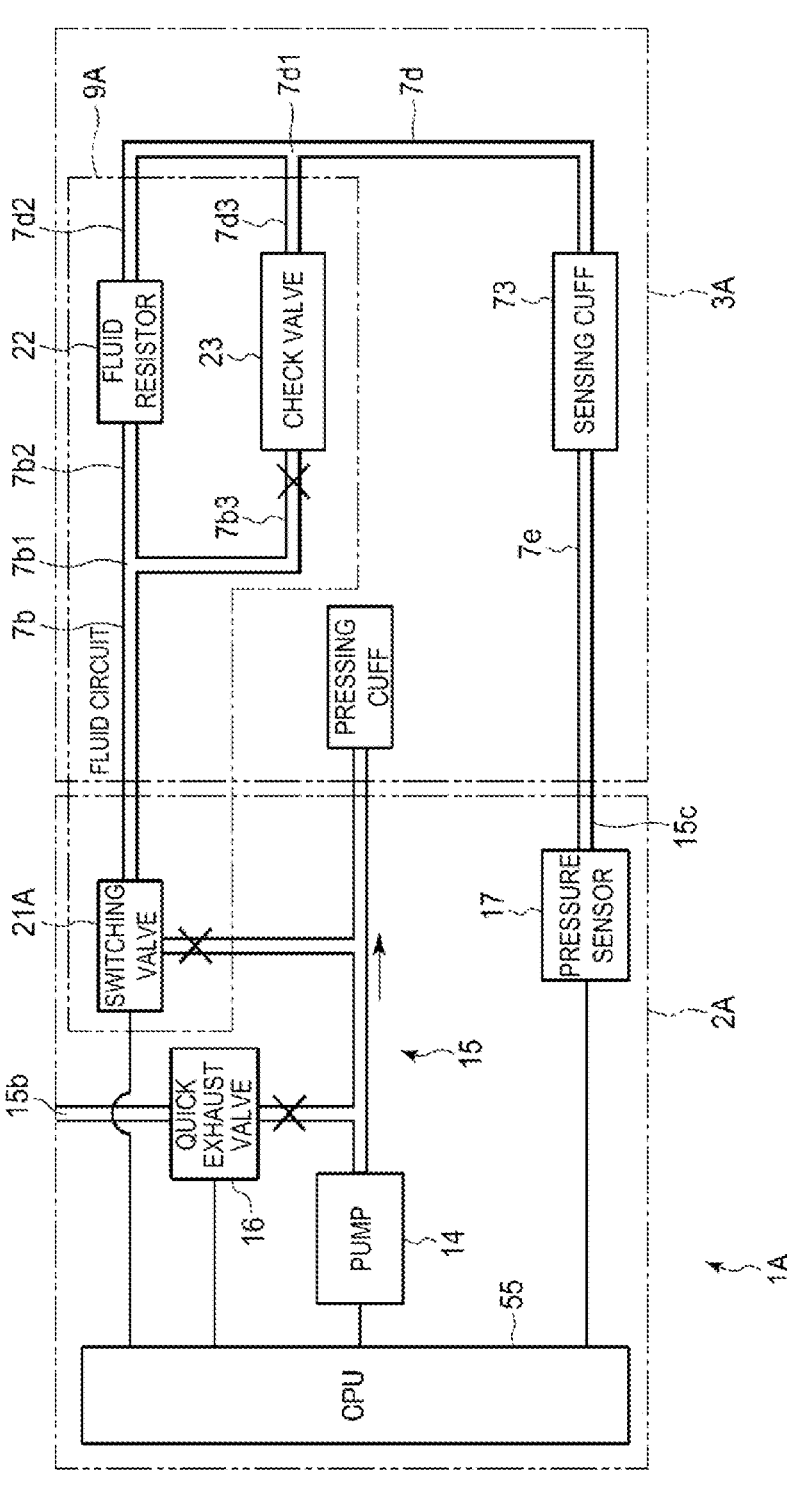
FIG. 10 is a block diagram illustrating the configuration of the blood pressure measurement device and illustrating an example of usage of the blood pressure measurement device.
Figure 11:
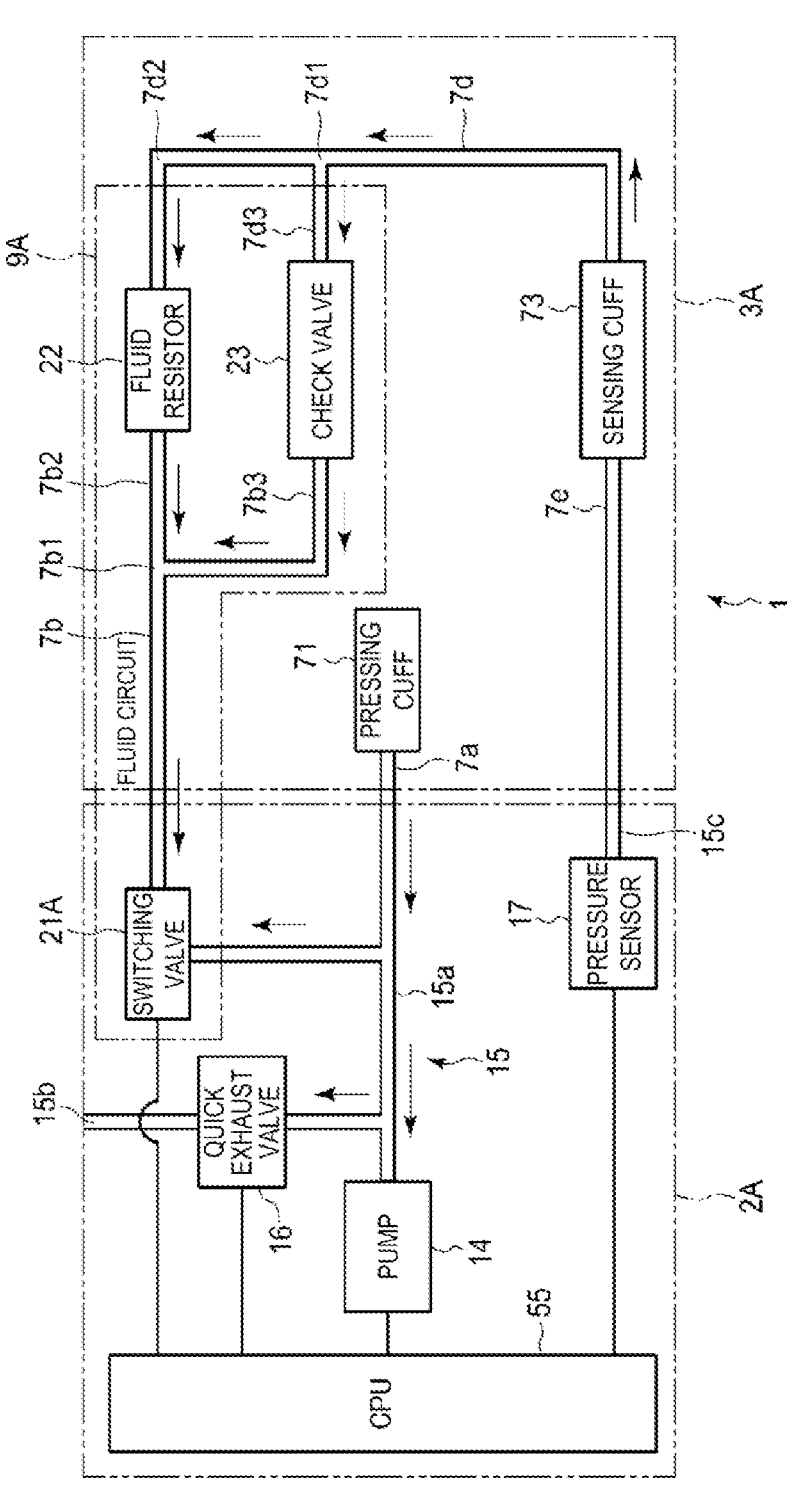
FIG. 11 is a block diagram illustrating the configuration of the blood pressure measurement device and illustrating an example of usage of the blood pressure measurement device.

Next, a blood pressure measurement device 1A according to the second embodiment will be described below with reference to FIG. 8 to FIG. 11. FIG. 8 is an explanatory view schematically illustrating a configuration of the blood pressure measurement device 1A according to the second embodiment. FIG. 9 and FIG. 10 are block diagrams illustrating the configuration of the blood pressure measurement device 1A and illustrating an example of a flow of a fluid supplied to each of the cuffs 71 and 73 in blood pressure measurement. FIG. 11 is a block diagram illustrating the configuration of the blood pressure measurement device 1 and illustrating an example of a flow of a fluid in exhaust of the fluid after blood pressure measurement. Note that in the blood pressure measurement device 1A according to the second embodiment, the same reference signs are given to configurations similar to those of the blood pressure measurement device 1 according to the first embodiment and detailed descriptions thereof are omitted.

As illustrated in FIG. 8, similar to the blood pressure measurement device 1, the blood pressure measurement device 1A is an electronic blood pressure measurement device attached to the living body 200. As illustrated in FIG.

8 to FIG. 11, the blood pressure measurement device 1 or 1A includes a device body 2A and a fluid circuit 3A.

The device body 2 includes the case 11, the display device 12, the operation device 13, the pump 14, the flow path unit 15, a first on-off valve (on-off valve) 16, the pressure sensor 17, the power supply unit 18, the communication device 19, the control substrate 20, and a second on-off valve 21A that achieves the function equivalent to the first valve by electrically opening and closing. That is, the device body 2A has a configuration including the second on-off valve 21A that electrically opens and closes as the first valve 21A and a configuration of the flow path 15a of the flow path unit 15 for connecting the second on-off valve 21A, which differ from the device body 2 of the first embodiment described above.

The case 11 houses, for example, the display device 12, the operation device 13, the pump 14, the flow path unit 15, the first on-off valve 16, the pressure sensor 17, the power supply unit 18, the communication device 19, the control substrate 20, and the second on-off valve 21A.

The flow path 15a of the flow path unit 15 forms a flow path from the pump 14 to a secondary side and branches a flow path from the pump 14 to the secondary side in three directions to connect to the pressing cuff 71, the first on-off valve 16, and the second on-off valve 21A.

The second on-off valve 21A is a switching valve controlled by the control unit 55 (the measurement processing unit 55a) to switch opening/closing of the flow path. The second on-off valve 21A is electrically connected to the control substrate 20. The second on-off valve 21A is controlled by the control substrate 20. For example, the second on-off valve 21A is opened and closed by control of the control substrate 20. The second on-off valve 21A is connected to the fluid resistor 22 and the second valve 23 of the fluid circuit 3A.

When air is supplied to the pressing cuff 71 and the sensing cuff 73 in the blood pressure measurement, the second on-off valve 21A switches to the open state to connect the pump 14 and the fluid resistor 22. That is, the second on-off valve 21A and the fluid resistor 22 constitute a fluid control unit 9A. Additionally, the second on-off valve 21A switches to the open state during exhaust to connect the pump 14 and the sensing cuff 73 and connect the sensing cuff 73 and the atmosphere.

The second on-off valve 21A is different from the first valve 21, which closes at the cracking pressure described above, in the configuration of being opened and closed by the control unit 55, but has an effect equivalent to that of the first valve 21 in terms of generating the function of the fluid control unit 9A.

For example, the storage unit 54 pre-stores, for example, program data for controlling the overall blood pressure measurement device 1A, the pump 14, the second on-off valve 21A, and the fluid circuit 3A, settings data for setting various functions of the blood pressure measurement device 1A, and calculation data for calculating a blood pressure value and a pulse from the pressure measured by the pressure sensor 17 to be changeable.

The control unit 55 controls the operation of the entire blood pressure measurement device 1A and the operations of the pump 14, the second on-off valve 21A, and the fluid circuit 3A based on the programs stored in the storage unit 54 to perform a predetermined operation (function). The control unit 55 is electrically connected to and supplies power to the display device 12, the operation device 13, the pump 14, the on-off valve 16, the pressure sensor 17, and the second on-off valve 21A. Additionally, the control unit 55 controls the operations of the display device 12, the pump 14, the on-off valve 16, and the second on-off valve 21A based on electrical signals output by the operation device 13 and the pressure sensor 17.

For example, a sub-CPU in the control unit 55 drives the pump 14, the on-off valve 16, and the second on-off valve 21A to feed compressed air to the fluid circuit 3A when an instruction to measure the blood pressure is input from the operation device 13. In addition, the sub-CPU controls driving and stop of the pump 14, opening and closing of the on-off valve 16, and the opening and closing of the second on-off valve 21A based on the electrical signal output by the pressure sensor 17. The sub-CPU controls the pump 14, the on-off valve 16, and the second on-off valve 21A to supply the compressed air to the fluid circuit 3A and selectively depressurize the fluid circuit 3A.

For example, the measurement processing unit 55a in the control unit 55 controls the pump 14, the on-off valve 16, and the second on-off valve 21A to supply air to the fluid circuit 3A, and calculates the blood pressure by an oscillometric method based on the pressure of the sensing cuff 73 detected by the pressure sensor 17.

The fluid circuit 3A includes the cuff structure 6, the tube group 7, the fluid resistor 22, and the second valve 23. The fluid resistor 22 and the second valve 23 of the fluid circuit 3A form the fluid control unit 9A together with the second on-off valve 21A. The fluid circuit 3A fluidly connects the cuff structure 6, the fluid resistor 22, and the second valve 23 by the tube group 7. The fluid circuit 3A is configured without the first valve 21 of the fluid circuit 3 in the blood pressure measurement device 1 according to the first embodiment described above.

The primary side of the second tube 7b of the tube group 7 is fluidly connected to the second on-off valve 21A. One branched tube portion 7b2 on the secondary side of the second tube 7b is connected to the fluid resistor 22. The tube portion 7b2 also serves as the tube 7c. The other branched tube portion 7b3 on the secondary side of the second tube 7b is connected to the second valve 23.

The second on-off valve 21A and the fluid circuit 3A exhibit the same functional effect as the fluid circuit 3 described above. Specifically, as illustrated in FIG. 9, when the supply of air is started by the pump 14 during blood pressure measurement, the air is supplied to the pressing cuff 71. Additionally, at the start of driving the pump 14, the measurement processing unit 55a in the control unit 55 sets the second on-off valve 21A in the open state. The second on-off valve 21A is in the open state, and the second valve 23 closes. Thus, as indicated by the arrows in FIG. 9, the air is also supplied to the sensing cuff 73 via the fluid resistor 22, in addition to the pressing cuff 71. At this time, as illustrated in FIG. 5, since the air supplied to the sensing cuff 73 passes through the fluid resistor 22, the amount of injection of air to the sensing cuff 73 is less than the amount of injection of air to the pressing cuff 71. Thus, as illustrated in FIG. 5, the increases in pressure of the pressing cuff 71 and the sensing cuff 73 differ, a relationship in which pressure of the pressing cuff 71 is higher than the pressure of the sensing cuff 73 is maintained, and the pressing cuff 71 and the sensing cuff 73 increase the pressures.

Then, when the pressure of the sensing cuff 73 reaches the desired pressure, the measurement processing unit 55a determines that the differential pressure between the pressure of the pressing cuff 71 and the pressure of the sensing cuff 73 reach a predetermined differential pressure. The measurement processing unit 55a controls the second on-off valve 21A to close the second on-off valve 21A. The air supplied by the pump 14 after the second on-off valve 21A closes is supplied to only the pressing cuff 71, as indicated by the arrows in FIG. 10. Thus, as illustrated in FIG. 5, after the second on-off valve 21A closes, the amount of injection of air to the pressing cuff 71 increases, but the amount of injection of air to the sensing cuff 73 does not increase. Note that, since the sensing cuff 73 is pressed to the living body 200 by the inflated pressing cuff 71, the amount of injection of air to the sensing cuff 73 does not change, but the pressure of the sensing cuff 73 increases. Accordingly, when air is supplied to the pressing cuff 71 and the sensing cuff 73 in blood pressure measurement, the pressures of the pressing cuff 71 and the sensing cuff 73 increase up to the pressures preferred for blood pressure measurement.

Further, when the exhaust of the fluid circuit 3A starts after the blood pressure measurement, the first on-off valve 16 is opened by the measurement processing unit 55a and the first on-off valve 16 side of the pressing cuff 71 is connected to the atmosphere, and thus, as illustrated in FIG. 11, the air in the pressing cuff 71 flows to the first on-off valve 16 side. As the exhaust of the pressing cuff 71 progresses, the pressure of the pressing cuff 71 decreases.

The measurement processing unit 55a opens the second on-off valve 21A simultaneously with the first on-off valve 16. As a result, the air in the sensing cuff 73 flows toward the first on-off valve 16 side via the fluid resistor 22 and the second on-off valve 21A. Note that the exhaust volume of the air exhausted from the sensing cuff 73 is reduced by the fluid resistor 22 and is smaller than the exhaust volume of air in the pressing cuff 71.

When the pressure of the pressing cuff 71 decreases and becomes lower than the pressure of the sensing cuff 73, as illustrated in FIG. 11, the second valve 23 opens, and as illustrated in FIG. 6, the quick exhaust of the sensing cuff 73 starts. Then, the exhaust of the pressing cuff 71 and the sensing cuff 73 proceeds, and the pressures of the pressing cuff 71 and the sensing cuff 73 become atmospheric pressures. Thus, the fluid circuit 3A is exhausted.

As an example, control during blood pressure measurement using the blood pressure measurement device 1A thus configured is performed in the flow same as an example of the control of the blood pressure measurement device 1 according to the above-described first embodiment illustrated in FIG. 7.

The blood pressure measurement device 1A thus configured produces effects similar to the effects of the blood pressure measurement device 1 according to the first embodiment described above. In other words, the blood pressure measurement device 1A includes the second on-off valve 21A (the first valve 21A) that opens and closes by the control by the control unit 55 and the fluid resistor 22 that lowers the amount of injection of air to the sensing cuff 73 than that of the pressing cuff 71. Thus, when air is supplied to the pressing cuff 71 and the sensing cuff 73 by the pump 14, the differential pressure is generated between the pressing cuff 71 and the sensing cuff 73. When the pressure of the sensing cuff 73 reaches a predetermined pressure, the control unit 55 closes the second on-off valve 21A, thus allowing the air to be injected into the sensing cuff 73 by the predetermined amount of injection. Accordingly, in blood pressure measurement, only control of the second on-off valve 21A may be performed in the step of the injection process of air by the measurement processing unit 55a in the control unit 55, shortening the measurement time. Therefore, an influence of artifact, such as body movement, is solved, and the blood pressure measurement device 1A improves in robustness in actual use.

In addition, in the injection process of air during blood pressure measurement, whether to close the second on-off valve 21A is determined by the pressure of air in the sensing cuff 73 detected by the pressure sensor 17. In addition, similar to the cracking pressure of the first valve 21 of the first embodiment described above, the pressure of the sensing cuff 73 when the second on-off valve 21A closes can be set by the preferred differential pressure between the pressing cuff 71 and the sensing cuff 73 and the resistance value of the fluid resistor 22 in blood pressure measurement. That is, the pressure of the sensing cuff 73 when the differential pressure between the sensing cuff 73 and the pressing cuff 71 whose amounts of injection of air are set by the fluid resistor 22 is the preferred differential pressure in blood pressure measurement may be set as a threshold value for determination whether to close the second on-off valve 21A. Furthermore, the threshold value is obtained in advance and stored in the storage unit 54.

Therefore, when the pressure of the sensing cuff 73 reaches the threshold value during blood pressure measurement, the measurement processing unit 55a only needs to perform the control of closing the second on-off valve 21A, and this facilitates the control of the second on-off valve 21A by the control unit 55. Thus, the blood pressure measurement device 1A can simplify the control in blood pressure measurement and reduce the power consumption. In addition, the valve for performing electrical control required for injection of air during blood pressure measurement may be the single second on-off valve 21A and can reduce the number of components required to be disposed on the device body 2A. Thus, the device body 2A can be miniaturized.

Additionally, in the blood pressure measurement device 1A, the second valve 23, which opens when the pressure of the pressing cuff 71 becomes lower than the pressure of the sensing cuff 73, is provided in parallel with the flow path passing through the first valve 21 and the fluid resistor 22. Thus, the air in the sensing cuff 73 is exhausted to the atmosphere via the pressing cuff 71 through the bypass path passing through the second valve 23, in addition to the flow path through the fluid resistor 22 and the first valve 21. Thus, the configuration including the fluid resistor 22 also allows preventing the reduction in exhaust speed of the sensing cuff 73. Additionally, the pressing cuff 71, which compresses the living body 200 more, is preferentially exhausted quickly, and when the pressure of the pressing cuff 71 falls below that of the sensing cuff 73, the second valve 23 opens, and thus an exhaust speed of the sensing cuff 73 increases. Thus, the blood pressure measurement device 1A can reduce a load on the living body due to the compression of the living body after the end of blood pressure measurement and the exhaust time of the sensing cuff 73 can be shortened.

As described above, according to the blood pressure measurement device 1A according to the second embodiment, the primary side of the pressing cuff 71 is branched, and the sensing cuff 73 is provided via the second on-off valve 21A and the fluid resistor 22. Thus, the blood pressure measurement device 1A allows controlling the amount of air injection to the sensing cuff 73 to be constant.

Third Embodiment

Next, a configuration of a blood pressure measurement device 1B according to the third embodiment will be described below with reference to FIG. 12 and FIG. 13. Note that the blood pressure measurement device 1B according to the third embodiment is an example in which the blood pressure measurement device 1 according to the first embodiment described above is applied to a wearable blood pressure measurement device attached to the wrist 200 as a living body. Among the configurations of the blood pressure measurement device 1B according to the third embodiment, the same reference signs are given to configurations similar to those of the blood pressure measurement device 1 according to the first embodiment described above and detailed descriptions thereof are omitted.

Figure 12:
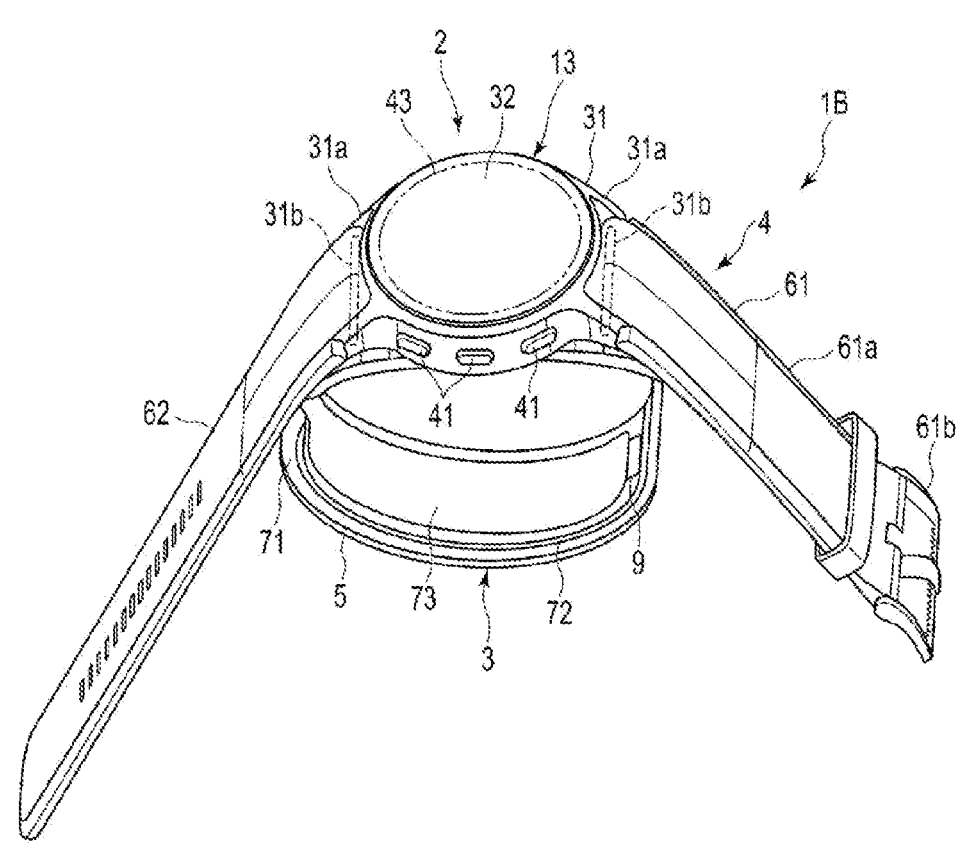
FIG. 12 is a perspective view illustrating a configuration of a blood pressure measurement device according to a third embodiment of the present invention.

As illustrated in FIG. 12, the blood pressure measurement device 1B includes the device body 2, the fluid circuit 3, the belt 4, which is a fixture that fixes the device body 2 to the wrist, and a curler 5 disposed between the belt 4 and the wrist 200.

As illustrated in FIG. 12, the case 11 of the device body 2 includes an outer case 31 and a windshield 32 covering an opening on the side opposite (outer side) from the wrist 200 side of the outer case 31. Additionally, the case 11 includes a rear cover provided on the wrist 200 side inside the outer case 31.

The outer case 31 is formed in a cylindrical shape. The outer case 31 includes pairs of lugs 31a provided at respective symmetrical positions in the circumferential direction of an outer circumferential surface, and spring rods 31b each provided between each of the two pairs of lugs 31a. The windshield 32 is, for example, a circular glass plate. Additionally, a base portion that supports each of the components is provided inside the outer case 31.

The display device 12 is disposed on the base portion of the outer case 31 and directly below the windshield 32.

The operation device 13 is configured to allow the user to input an instruction. As illustrated in FIG. 12, for example, the operation device 13 includes a plurality of buttons 41 provided on the case 11, a sensor that detects the operation of the buttons 41, and a touch panel 43 provided on the display device 12 or the windshield 32. When operated by the user, the operation device 13 converts an instruction into an electrical signal. The sensor and the touch panel 43 are electrically connected to the control substrate 20 to output electrical signals to the control substrate 20.

As illustrated in FIG. 12, the belt 4 includes a first belt 61 provided on one of the pair of lugs 31a and the spring rod 31b, a second belt 62 provided on the other pair of lugs 31a and the spring rod 31b, and a connector that connects the first belt 61 and the second belt 62. The belt 4 is wrapped around the wrist 200 with the curler 5 in between. Note that in the present embodiment, the connector is a buckle 61b provided to the first belt 61.

The first belt 61 is referred to as a so-called a parent and is configured like a band capable of being joined to the second belt 62. As illustrated in FIG. 12, the first belt 61 includes a belt portion 61a and the buckle 61b. The belt portion 61a is configured like a band. The belt portion 61a is formed of an elastically deformable resin material. In addition, the belt portion 61a is flexible and includes a sheet-like insert member inside the belt portion 61a for suppressing stretching in the longitudinal direction of the belt portion 61a.

The belt portion 61a is provided with the spring rod 31b at one end portion and the buckle 61b at the other end portion. The spring rod 31b provided on the one end portion of the first belt 61 is disposed between the pair of lugs 31a, and thus the first belt 61 is rotatably held to the outer case 31.

The second belt 62 is referred to as so-called tip of a blade and formed like a band. The second belt 62 is formed of an elastically deformable resin material. In addition, the second belt 62, for example, is flexible and includes a sheet-like insert member inside the second belt 62 for suppressing stretching in the longitudinal direction of the second belt 62.

The second belt 62 is fixed to the buckle 61b. The second belt 62 is provided with the spring rod 31b at one end portion. The spring rod 31b provided on the one end portion of the second belt 62 is disposed between the pair of lugs 31a, and thus the second belt 62 is rotatably held to the outer case 31.

Thus, the first belt 61 and the second belt 62 of the belt 4 are integrally connected together by the buckle 61b, and the belt 4 comes to have an annular shape following along the circumferential direction of the wrist 200 along with the outer case 31. By shaping the belt 4 in an annular shape following along the circumferential direction of the wrist, the curler 5 is pressed and elastically deformed to follow along the circumferential direction of the wrist of the wearer of a blood pressure measurement device 1B.

As illustrated in FIG. 12, the curler 5 is configured in a band-like shape that curves in such a manner as to follow along the circumferential direction of the wrist 200. The curler 5 is formed with a first end and a second end spaced apart from each other. For example, the outer surface on the first end side of the curler 5 is fixed to the rear cover side of the device body 2 or is integrally formed with the rear cover of the device body 2 and the base portion. The curler 5 is disposed, for example, at a position where the first end and the second end protrude more to one side of the wrist 200 than the device body 2. Accordingly, the curler 5 is disposed with the first end and the second end to the side of the wrist 200 when the blood pressure measurement device 1B is attached to the wrist 200. Furthermore, the first end and the second end of the curler 5 are located adjacent to each other at a predetermined distance from each other. The curler 5 is formed of a resin material, for example.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist. In the curler 5, the cuff structure 6 is disposed on the inner circumferential surface.

For example, in the fluid circuit 3, the cuff structure 6, the tube group 7, and the fluid control unit 9 are integrally formed. For example, the fluid circuit 3 is configured by integrally incorporating the tube group 7 and the fluid control unit 9 into a portion of the cuff structure 6.

Figure 13:
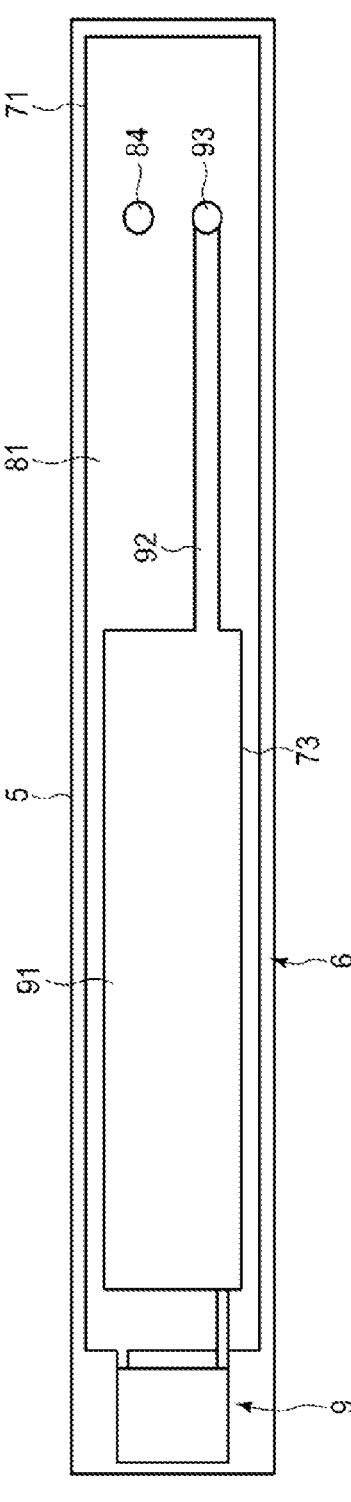
FIG. 13 is a plan view illustrating a configuration of a cuff structure and a fluid control unit of the blood pressure measurement device.

As a specific example, as illustrated in FIG. 12 and FIG. 13, the cuff structure 6 includes the pressing cuff 71, the sensing cuff 73, and the fluid control unit 9. FIG. 13 is a developed view illustrating the configuration of the curler 5 and the cuff structure 6. In the cuff structure 6, the pressing cuff 71 and the sensing cuff 73 are stacked and fixed in this order from the inner peripheral surface of the curler 5 to the wrist side, on the inner peripheral surface on the hand palm side of the wrist of the curler 5.

The cuff structure 6 includes a back plate 72 that supports the sensing cuff 73 between the pressing cuff 71 and the sensing cuff 73, for example. As a specific example, the back plate 72 is formed to have a length so as to cover the hand palm side of the wrist 200. The back plate 72 transmits the pressing force from the pressing cuff 71 to the main surface on the back plate 72 side of the sensing cuff 73 in a state in which the back plate 72 runs along the shape of the wrist.

The pressing cuff 71 is set to, for example, substantially the same length as the length in the longitudinal direction of the curler 5. The pressing cuff 71 includes a plurality of, for example, two-layer air bags 81 and a connection portion 84 provided on the first end side in the longitudinal direction. The pressing cuff 71 is provided with the fluid control unit 9 on the second end side in the longitudinal direction.

Here, the air bag 81 has a bag-like structure. The plurality of air bags 81 are stacked and are in fluid communication with one another in the stacking direction. Each of the air bags 81 is formed in a rectangular bag-like shape that is long in one direction. Additionally, the air bag 81 is set such that the width in the lateral direction is the same as or slightly smaller than the width in the lateral direction of the curler 5. The air bag 81 is formed by, for example, combining two sheet members and thermally welding the sheet members in a rectangular frame shape long in one direction using heat. In addition, the two-layer air bags 81 are formed by integrally combining the two air bags 81 by welding using heat, or welding the facing sheet members of the adjacent air bags 81 and after that welding the air bags 81.

The connection portion 84 is, for example, a nipple. The connection portion 84 protrudes from the air bag 81. The connection portion 84 is the first tube 7a connected to the flow path unit 15.

The sensing cuff 73 is, for example, set to have a length such that the sensing cuff 73 can be disposed in a region where the artery is present in the wrist. The sensing cuff 73 faces the region where the artery is present in the wrist with the blood pressure measurement device 1B attached to the wrist. The artery as used herein is a radial artery and/or an ulnar artery. The sensing cuff 73 is inflated to compress the region where the artery on the hand palm side is present in the wrist. The sensing cuff 73 is pressed by the inflated pressing cuff 71 to the wrist side.

As a specific example, the sensing cuff 73 includes one air bag 91, a flow path body 92 that communicates with the air bag 91, and a connection portion 93 provided at the leading end of the flow path body 92. The sensing cuff 73 is constituted by integrally welding two sheet members.

The air bag 91 is constituted in a rectangular shape that is long in one direction. The air bag 91 is, for example, set to have a length such that the air bag 91 can be disposed in a region where the artery is present in the wrist. The air bag 91 is formed by, for example, combining two sheet members long in one direction and thermally welding the sheet members in a rectangular frame shape long in one direction using heat.

The flow path body 92 is integrally provided at a portion of one edge portion of the air bag 91 in the longitudinal direction. As a specific example, the flow path body 92 is provided at the end portion of the air bag 91 near the device body 2. Additionally, the flow path body 92 is, for example, formed in a shape that is long in one direction, has a width smaller than the width of the air bag 91 in the lateral direction, and is formed with a leading end having a circular shape. The flow path body 92 includes the connection portion 93 on the leading end.

The flow path body 92 is constituted by welding the two sheet members in a frame shape long in one direction using heat, in a state where the connection portion 93 is disposed on the two sheet members. Note that, portions of the weld portions where the two sheet members are welded in a rectangular frame shape are not welded and the air bag 91 is constituted to be continuous with a weld portion forming the flow path body 92, and thus the air bag 91 fluidly continues with the flow path body 92.

The connection portion 93 is, for example, a nipple. The connection portion 93 is provided at the leading end of the flow path body 92. Also, the leading end of the connection portion 93 is externally exposed from the sheet member on the side of facing the curler 5 among the two sheet members constituting the flow path body 92. The connection portion 93 is connected to the flow path unit 15.

Thus, the flow path body 92 and the connection portion 93 are connected to the flow path unit 15 via the connection portion 93, and constitute the fifth tube 7e that connects the air bag 91 and the pressure sensor 17.

In the cuff structure 6 configured in this manner, the pressing cuff 71 includes the first tube 7a of the tube group 7 and the sensing cuff 73 includes the fifth tube 7e.

The fluid control unit 9 is disposed, for example, on an inner surface of the curler 5 and at an end portion on the hand palm side of the wrist. The fluid control unit 9 is integrally formed with the end portions of the pressing cuff 71 and the sensing cuff 73. As a specific example, the fluid control unit 9 is integrally formed with the end portion of the pressing cuff 71 and a portion of which is fluidly connected to the sensing cuff 73.

For example, the fluid control unit 9 includes the second tube 7b, the third tube 7c, the fourth tube 7d, the first valve 21, the fluid resistor 22, and the second valve 23. In the fluid control unit 9, the second tube 7b, the third tube 7c, the fourth tube 7d, the first valve 21, the fluid resistor 22, and the second valve 23 are integrally formed.

The second tube 7b, the third tube 7c, and the fourth tube 7d are formed by, for example, a portion of a pair of the seat members constituting one air bag 81 of the pressing cuff 71. For example, the second tube 7b, the third tube 7c, and the fourth tube 7d are clearances formed between the pair of seat members by not welding the regions constituting the second tube 7b, the third tube 7c, and the fourth tube 7d when the pair of sheet members are welded. The first valve 21, the fluid resistor 22, and the second valve 23 are disposed in the clearances between the pair of sheet members constituting the second tube 7b, the third tube 7c, and the fourth tube 7d. Further, the secondary side of the joint portion 7d1 of the fourth tube 7d is connected to the sensing cuff 73.

The blood pressure measurement device 1B thus configured produces effects similar to the effects of the blood pressure measurement device 1 according to the first embodiment described above. In addition, in the blood pressure measurement device 1B, the second tube 7b, the third tube 7c, the fourth tube 7d, the first valve 21, the fluid resistor 22, and the second valve 23 are integrally formed to form the fluid control unit 9, and the fluid control unit 9 is integrally connected to the end portions of the pressing cuff 71 and the sensing cuff 73. The fluid control unit 9 is configured to be disposed at the end portion of the curler 5. In the blood pressure measurement device 1B, the fluid control unit 9 can be disposed integrally with the pressing cuff 71 and the sensing cuff 73 on the curler 5. This eliminates the need for disposing the fluid control unit 9 in the device body 2 and allows miniaturizing the device body 2. In addition, since the fluid control unit 9 is disposed on the end portion of the curler 5, it is possible to prevent the fluid control unit 9 from inhibiting blood pressure measurement during blood pressure measurement.

Other Embodiments

Figure 14:
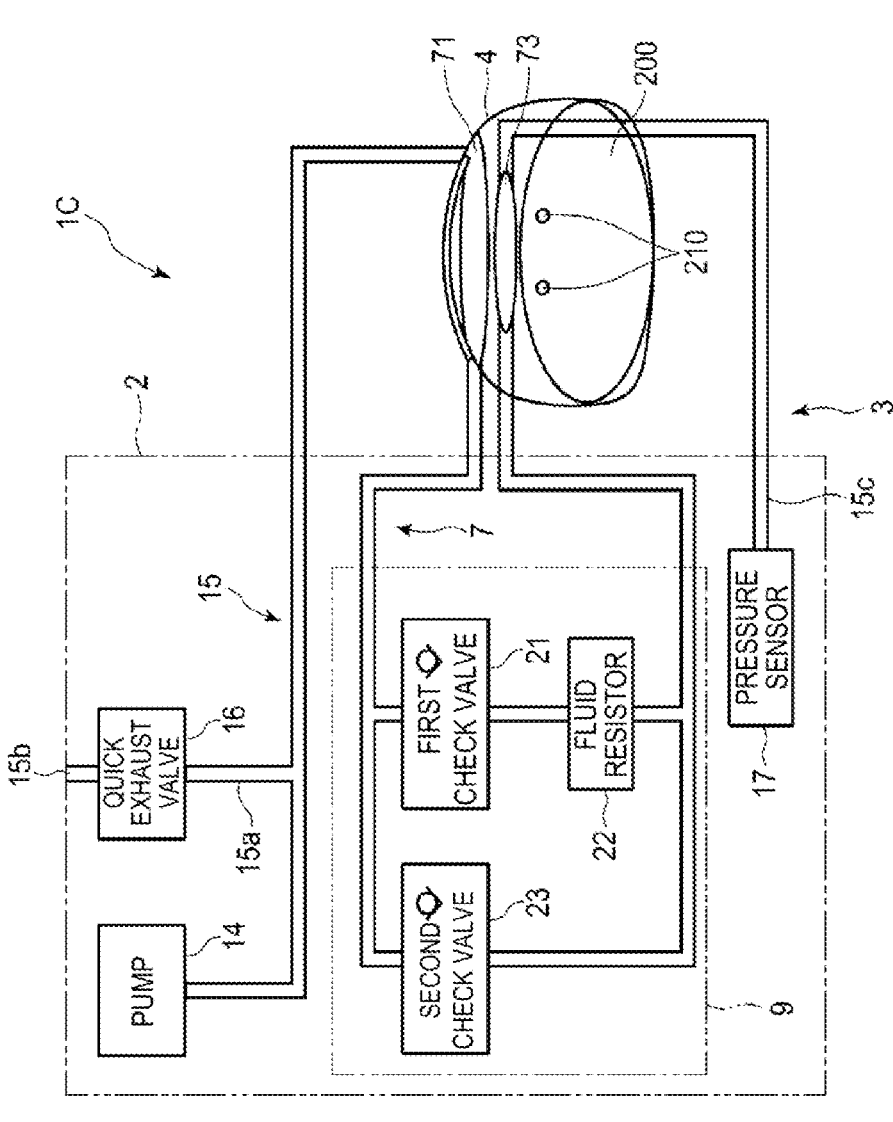
FIG. 14 is an explanatory view schematically illustrating a configuration of a blood pressure measurement device according to a fourth embodiment of the present invention.

Note that the present invention is not limited to the embodiments described above. For example, in the examples described above, in the blood pressure measurement device 1, 1A, or 1B according to each of the embodiments, an example in which the fluid circuit 3 or 3A is disposed outside the device body 2 has been described, but the configuration is not limited to this. For example, the blood pressure measurement device 1 or 1A may be configured to house a portion of the configuration of the fluid circuit 3 or 3A in the device body 2. As a specific example, like a blood pressure measurement device 1C according to a fourth embodiment illustrated in FIG. 14, for example, among the configurations of the fluid circuit 3, the first valve 21, the fluid resistor 22, and the second valve 23 constituting the fluid control unit 9 and a portion of the tube group 7 for fluidly connecting them to another configuration may be housed in the device body 2. For example, in this example, the second tube 7b, the third tube 7c, and the fourth tube 7d are housed in the device body 2.

Figure 15:
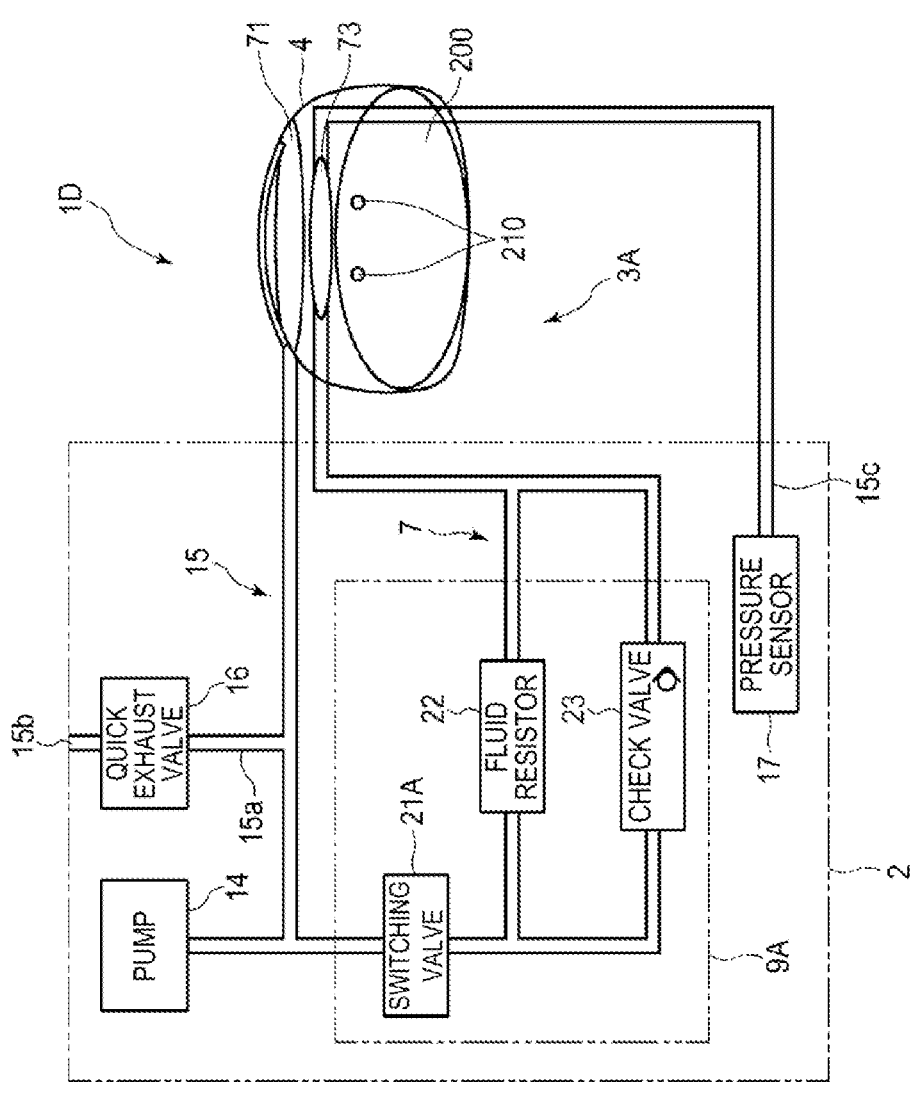
FIG. 15 is an explanatory view schematically illustrating a configuration of a blood pressure measurement device according to a fifth embodiment of the present invention.

Similarly, as a specific example, like a blood pressure measurement device 1D according to a fifth embodiment illustrated in FIG. 15, for example, among the configurations of the fluid circuit 3A, the first valve 21A, the fluid resistor 22, and the second valve 23 constituting the fluid control unit 9A and a portion of the tube group 7 for fluidly connecting them to another configuration may be housed in the device body 2. In this example, for example, the second tube 7b and the fourth tube 7d are housed in the device body 2.

In addition, in the example described above, as an example of applying the blood pressure measurement device 1 according to the first embodiment to the wearable blood pressure measurement device attached to the wrist 200, the blood pressure measurement device 1B according to the third embodiment has been described, but the configuration is not limited thereto. For example, the blood pressure measurement device 1A according to the second embodiment may be applied to a wearable blood pressure measurement device equivalent to the wearable blood pressure measurement device 1B according to the third embodiment. In such a case, the second on-off valve 21A (the first valve 21A) may be housed in the case 11, and among the configurations of the fluid control unit 9A, the fluid resistor 22, the second valve 23, and each of tubes 7b and 7d may be integrally formed at the respective end portions of the pressing cuff 71 and the sensing cuff 73.

Figure 16:
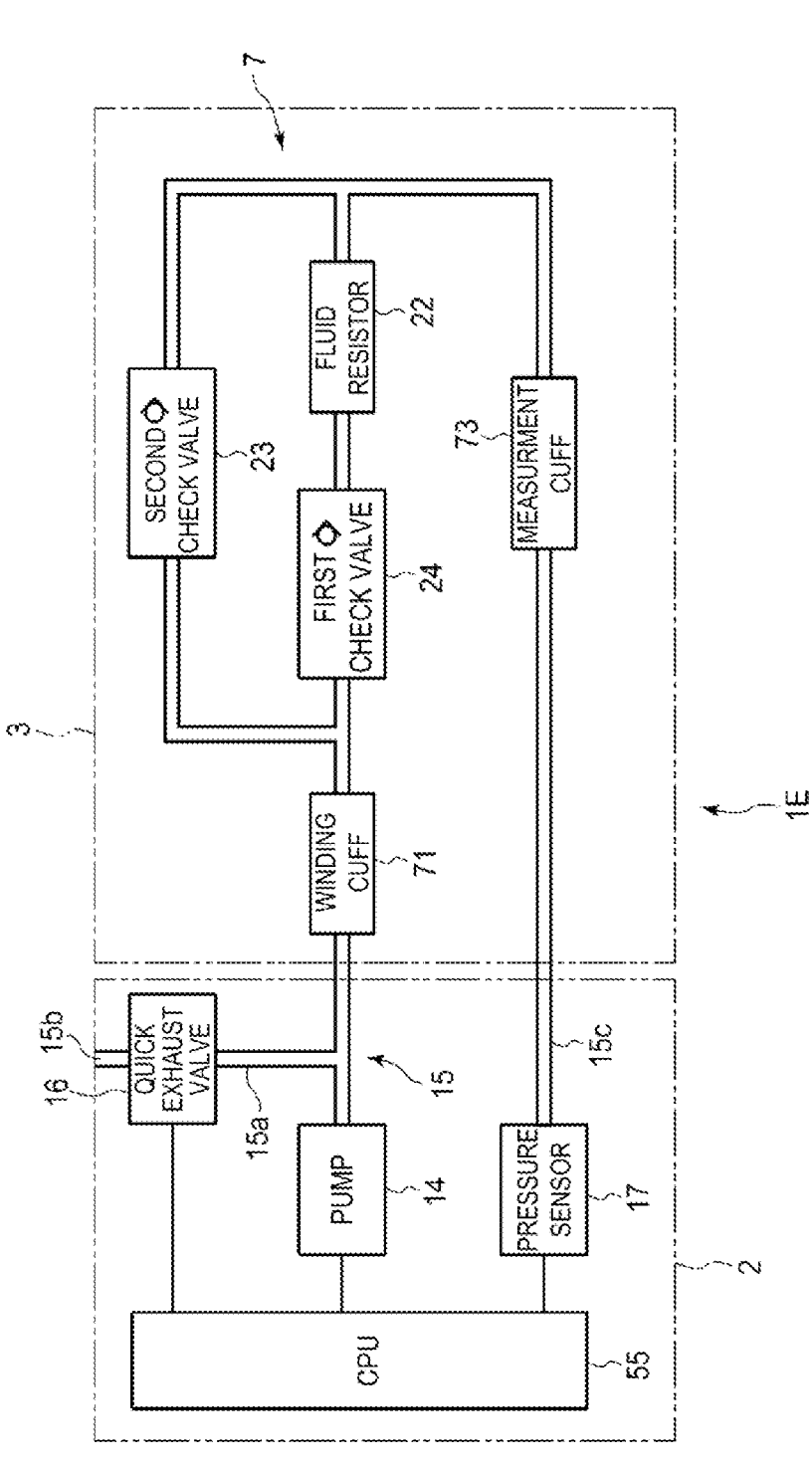
FIG. 16 is an explanatory view schematically illustrating a configuration of a blood pressure measurement device according to a sixth embodiment of the present invention.

The blood pressure measurement device 1 or 1A may be configured to be attached to an upper arm. In such a configuration, in the blood pressure measurement device 1 or 1A, the first cuff 71 may be used as the winding cuff 71 that is wound around the upper arm and the second cuff 73 may be used as the measurement cuff 73. For example, FIG. 16 illustrates an example of a blood pressure measurement device 1E attached to the upper arm according to a sixth embodiment. Note that similarly, in the blood pressure measurement device 1E attached to the upper arm as well, the first cuff 71 may be used as the winding cuff. In addition, in the case of the blood pressure measurement device 1 or 1A attached to the upper arm, an automatic winding function may be provided.

Additionally, the blood pressure measurement device 1, 1A, or 1B described above has been described with a reduced pressure measurement method as an example of blood pressure measurement, but the method is not limited thereto. Each of the blood pressure measurement devices 1, 1A, and 1B may employ a pressurization measurement method as an example of blood pressure measurement. In the case of the blood pressure measurement device 1, 1A, or 1B of the pressure measurement method, as a blood pressure measurement device according to a seventh embodiment, the on-off valve 16 may be a quick exhaust valve that allows quick exhaust and the blood pressure may be measured by pressurization measurement method.

Figure 17:
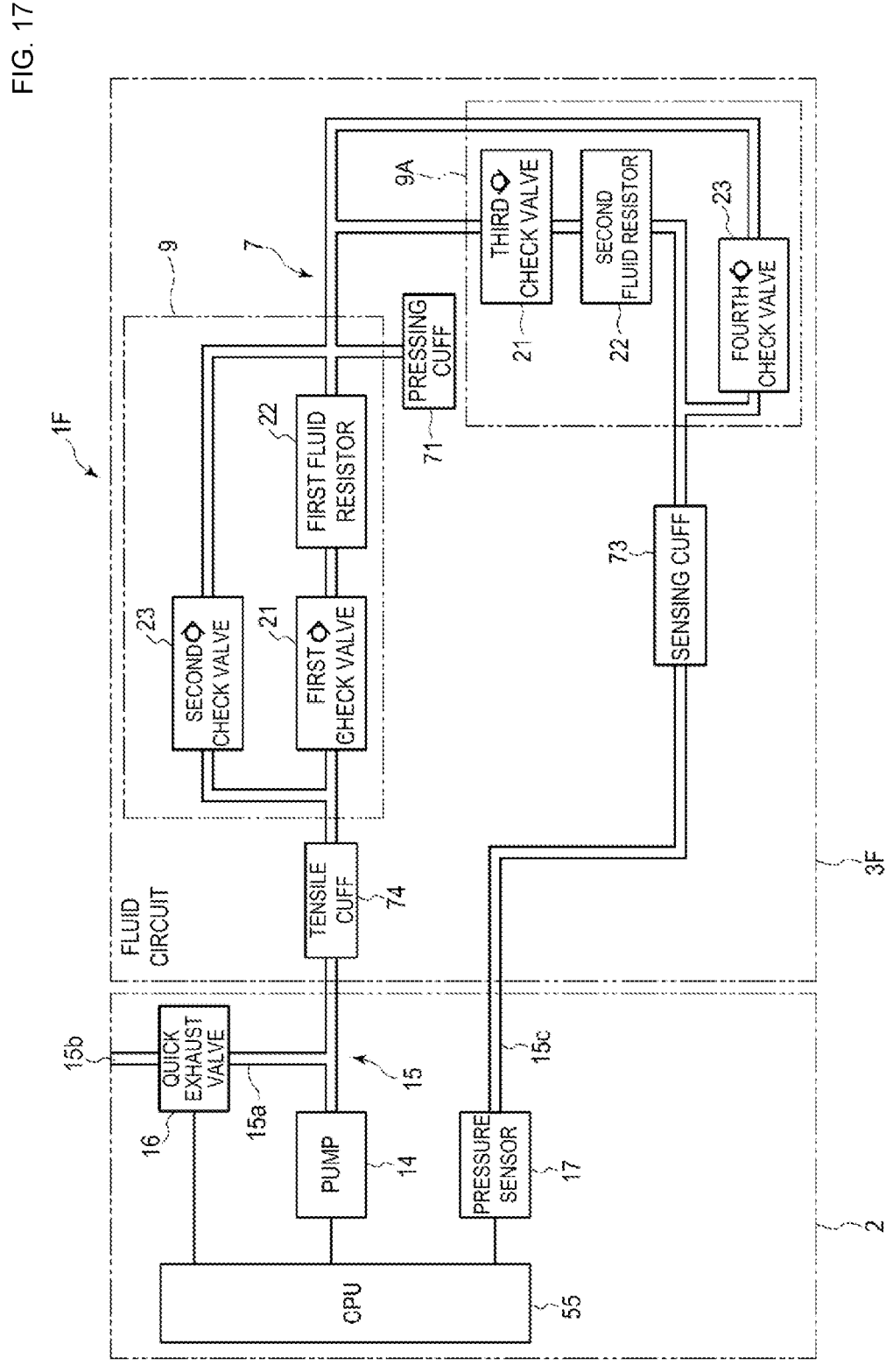
FIG. 17 is an explanatory view schematically illustrating a configuration of a blood pressure measurement device according to an eighth embodiment of the present invention.

Additionally, in the examples described above, the configuration in which the blood pressure measurement device 1, 1A, or 1B includes the two cuffs 71 and 73 has been described, but the configuration is not limited to this. That is, the blood pressure measurement device 1 or 1A may include three or more cuffs and be configured to provide the respective fluid control units 9 or 9A between the two cuffs. For example, as illustrated in FIG. 17 as an example, in the case of the three cuffs, in addition to the pressing cuff 71 and the sensing cuff 73, for example, a tensile cuff 74 as a third cuff 74 provided on a hand back side of the wrist and inflating to pull the side of the hand of the wrist and an assist cuff that presses the hand back side of the wrist can be provided. Additionally, the four or more cuffs may be used. The respective fluid control units 9 or 9A may be provided between the tensile cuff 74 and the pressing cuff 71 and between the pressing cuff 71 and the sensing cuff 73. The pressure (the differential pressure) and the resistance value of the fluid resistor at which the respective valves of the plurality of fluid control units 9 and 9A open and close are appropriately set such that the amount of injection of the cuff on the secondary side becomes constant. FIG. 17 illustrates an example of providing the two fluid control units 9 and 9A in a fluid circuit 3F as an example of a blood pressure measurement device 1F according to an eighth embodiment. Note that in FIG. 17, the first valve (first check valve) 21 of the fluid control unit 9A on the secondary side is referred to as the third check valve 21, the fluid resistor 22 is referred to as the second fluid resistor 22, and the second valve (the second check valve) 23 is referred to as the fourth check valve 23.

Further, when the blood pressure measurement device 1, 1A, or 1B is configured to include the three or more cuffs, the fluid control units 9 or 9A (first fluid control units) for controlling the amount of injection are provided between the two cuffs, and a second fluid control unit 9G that controls a pressure ratio may be provided between the other two cuffs. Next, a blood pressure measurement device 1G according to a ninth embodiment will be described below with reference to FIG. 18. Among the configurations of the blood pressure measurement device 1G, the same reference signs are given to configurations similar to those of the blood pressure measurement device according to each of the embodiments described above and detailed descriptions thereof are omitted.

The blood pressure measurement device 1G includes the device body 2 and a fluid circuit 3G. The fluid circuit 3G includes the cuff structure 6, the tube group 7, the first fluid control unit 9, and the second fluid control unit 9G. The first fluid control unit 9 may be the fluid control unit 9A described above. The cuff structure 6 includes the pressing cuff 71 as the first cuff 71, the sensing cuff 73 as the second cuff 73, and the tensile cuff 74 as the third cuff 74. For example, the tensile cuff 74 includes the number of air bags larger than that of the pressing cuff 71 and inflates more than the pressing cuff 71. That is, the tensile cuff 74 is set to be larger in volume during inflation than those of the pressing cuff 71 and the sensing cuff 73. For example, the tensile cuff 74 is provided on the primary side (the pump 14 side) than the pressing cuff 71. In a case where a plurality of cuffs are provided, for example, a cuff having a large volume during inflation is disposed on the pump 14 side of the fluid circuit.

Figure 18:
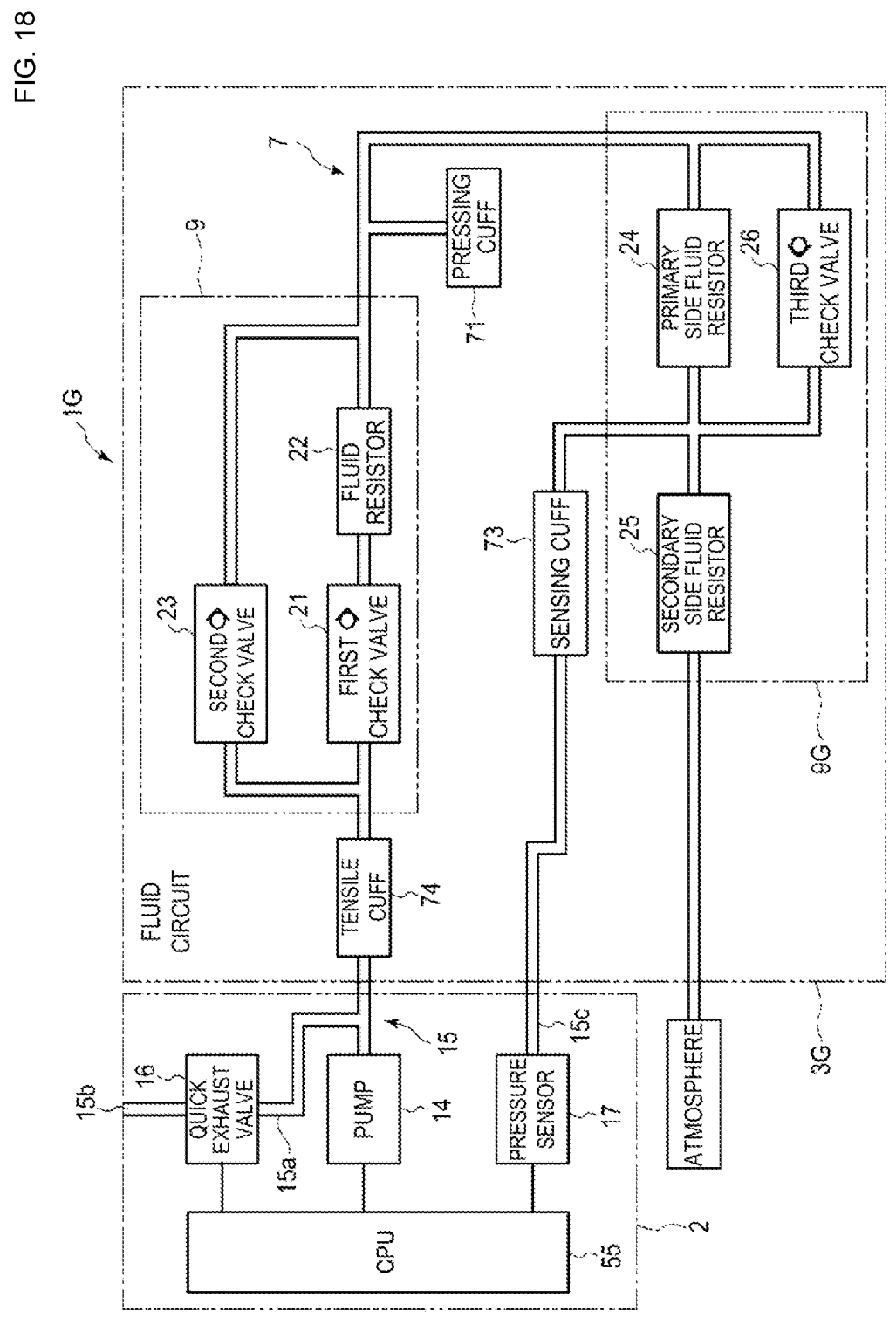
FIG. 18 is an explanatory view schematically illustrating a configuration of a blood pressure measurement device according to a ninth embodiment of the present invention; and, FIG. 19 is an explanatory view schematically illustrating a configuration of a blood pressure measurement device according to a tenth embodiment of the present invention.

As illustrated in FIG. 18, the first fluid control unit 9 is provided between the tensile cuff 74 and the pressing cuff 71, for example.

The second fluid control unit 9G controls a pressure ratio of the air between the two cuffs so as to be constant by a fluid resistance ratio between the two fluid resistors 24 and 25. As illustrated in FIG. 18, the second fluid control unit 9G is provided between the pressing cuff 71 and the sensing cuff 73, for example.

As a specific example, the second fluid control unit 9G includes a primary side fluid resistor 24, a secondary side fluid resistor 25, and a third valve 26.

The primary side fluid resistor 24 provides a resistance of the passing fluid, air in the present embodiment. The primary side fluid resistor 24 has, for example, a flow path cross-sectional area smaller than flow path cross-sectional areas on the primary side and the secondary side of the primary side fluid resistor 24, that is, flow path cross-sectional areas of the second tube 7b and the third tube 7c. The primary side fluid resistor 24 is, for example, an orifice. The primary side fluid resistor 24 reduces the flow path on the flow path from the pressing cuff 71 to the sensing cuff 73 to lower a flow rate of air supplied to the secondary side of the primary side fluid resistor 24 than a flow rate of air supplied to the pressing cuff 71.

The secondary side fluid resistor 25 provides a resistance of the passing fluid, air in the present embodiment. The secondary side fluid resistor 25 has, for example, a flow path cross-sectional area smaller than flow path cross-sectional areas on the primary side and the secondary side of the secondary side fluid resistor 25, that is, flow path cross-sectional areas of the second tube 7b and the third tube 7c. The secondary side fluid resistor 25 is, for example, an orifice. The secondary side fluid resistor 25 reduces the flow path on the flow path from the flow path between the primary side fluid resistor 24 and the secondary side fluid resistor 25 to the atmosphere to lower a flow rate of air supplied to the secondary side (the atmosphere) of the secondary side fluid resistor 25 than a flow rate of air supplied to the primary side fluid resistor 24 and the secondary side fluid resistor 25. That is, when a portion of the air supplied to the flow path between the primary side fluid resistor 24 and the secondary side fluid resistor 25 flows to the sensing cuff 73 and the atmosphere, the secondary side fluid resistor 25 provides a resistance of air flow toward the atmosphere side, and controls the flow rate of air injected into the sensing cuff 73 and the flow rate of air flowing out to the atmosphere.

For a fluid resistance ratio between the primary side fluid resistor 24 and the secondary side fluid resistor 25, for example, by experimentally obtaining a relationship between the fluid resistance ratio between the primary side fluid resistor 24 and the secondary side fluid resistor 25 and a measurement error, the optimal fluid resistance ratio is set. As a specific example, the blood pressure is measured multiple times with the fluid resistance ratios between the primary side fluid resistor 24 and the secondary side fluid resistor 25 differentiated, the respective measurement errors are obtained, and the optimal fluid resistance ratio is estimated from the blood pressure measurement errors. For example, assume that the blood pressure error is approximately 5 mm Hg with a first fluid resistance ratio (the primary side fluid resistor 24/the secondary side fluid resistor 25) of 0.67 and the blood pressure error is approximately −15 mm Hg with a second fluid resistance ratio of 1. From the relationship, the optimal fluid resistance ratio where the blood pressure error becomes 0 mm Hg can be estimated as 0.75. Then, the primary side fluid resistor 24 and the secondary side fluid resistor 25 to meet the fluid resistance ratio are set. Note that the relationship of the fluid resistance ratio between the primary side fluid resistor 24 and the secondary side fluid resistor 25 changes depending on the compression force by the cuffs 71 and 73 of the blood pressure measurement device 1G, and therefore adjustment is performed according to the properties of the cuffs 71 and 73.

The third valve 26 opens when the pressure on the primary side is lower than the pressure on the secondary side. Specifically, the third valve 26 closes when the pressure on the pressing cuff 71 side is equal to or more than the pressure on the flow path (the sensing cuff 73) side between the primary side fluid resistor 24 and the secondary side fluid resistor 25 and opens when the pressure on the pressing cuff 71 side is lower than the pressure on the flow path side (the sensing cuff 73 side) between the primary side fluid resistor 24 and the secondary side fluid resistor 25. The third valve 26, for example, always closes during blood pressure measurement and opens when the differential pressure between the pressure of the pressure of the pressing cuff 71 and the pressure of the sensing cuff 73 is eliminated during exhaust while the pressure of the pressing cuff 71 becomes a cracking pressure in which the pressure of the pressing cuff 71 falls below the pressure of the sensing cuff 73. The third valve 26 is, for example, a check valve.

For example, a cracking pressure of the third valve 26 is set to a preferred pressure for exhaust of the pressing cuff 71 and the sensing cuff 73, for example. As a specific example, the cracking pressure of the third valve 26 is set to 0 mm Hg such that the third valve 26 opens when the pressure of the pressing cuff 71 falls below the pressure of the sensing cuff 73.

Note that the third valve 26 is configured to prevent the air in the pressing cuff 71 from flowing toward the sensing cuff 73 side during exhaust, and open when the pressure on the primary side is lower than the pressure on the secondary side. However, when the air does not substantially flow from the pressing cuff 71 to the sensing cuff 73 in exhaust of the fluid circuit 3G, the third valve 26 may be set to have the cracking pressure in which the third valve 26 opens when the pressure on the primary side is slightly higher than the pressure on the secondary side.

The fluid circuit 3G including the first fluid control unit 9 and the second fluid control unit 9G is connected by the tube group 7 as follows. That is, the pressing cuff 71 is provided on the secondary sides of the first fluid resistor 22 and the second valve 23. Further, the primary side fluid resistor 24 and the secondary side fluid resistor 25 are provided on the secondary side of the pressing cuff 71, and the sensing cuff 73 is connected to a flow path between the primary side fluid resistor 24 and the secondary side fluid resistor 25. The third valve 26 is connected to the secondary side of the pressing cuff 71 in parallel with the primary side fluid resistor 24.

In the fluid circuit 3G, the on-off valve 16 is closed by the measurement processing unit 55a in the control unit 55 during blood pressure measurement, and when the pump 14 starts driving, the air is first supplied to the tensile cuff 74. At this time, the first valve 21 opens. Since the air is first supplied to the tensile cuff 74, the second valve 23 closes. Thus, the air supplied to the tensile cuff 74 is supplied to the pressing cuff 71 side via the first valve 21 and the fluid resistor 22. At this time, since the air supplied to the pressing cuff 71 passes through the fluid resistor 22, the amount of injection of air to the pressing cuff 71 side is less than the amount of injection of air to the tensile cuff 74 side. Thus, the increases in pressure of the tensile cuff 74 and the pressing cuff 71 differ, and a relationship in which pressure of the tensile cuff 74 is higher than the pressure of the pressing cuff 71 is maintained, and the tensile cuff 74 and the pressing cuff 71 increase the pressures.

Additionally, the air passing through the first fluid resistor 22 from the tensile cuff 74 increases the pressure on the primary side of the third valve 26 to be higher than the pressure on the secondary side, and the third valve 26 closes. Then, a portion of the air that passes through the first fluid resistor 22 from the tensile cuff 74 and is supplied to the pressing cuff 71 side is supplied to the pressing cuff 71, and the other air passes through the primary side fluid resistor 24 and is supplied to the flow path between the primary side fluid resistor 24 and the secondary side fluid resistor 25. At this time, the amount of injection of the air supplied to the pressing cuff 71 becomes larger than the amount of injection of the air supplied to the flow path between the primary side fluid resistor 24 and the secondary side fluid resistor 25 due to the resistance of the primary side fluid resistor 24.

A portion of the air supplied to the flow path between the primary side fluid resistor 24 and the secondary side fluid resistor 25 is injected into the sensing cuff 73, and the other air supplied to the flow path between the primary side fluid resistor 24 and the secondary side fluid resistor 25 passes through the secondary side fluid resistor 25 and is exhausted to the atmosphere. At this time, due to the resistance of the secondary side fluid resistor 25, the flow rate of the air flowing to each of the sensing cuff 73 and the atmosphere changes in the air supplied to the flow path between the primary side fluid resistor 24 and the secondary side fluid resistor 25.

In addition, since the fluid resistance ratio between the primary side fluid resistor 24 and the secondary side fluid resistor 25 is set, the pressure ratio between the pressure of the pressing cuff 71 and the pressure of the sensing cuff 73 is constant from the start of supply of the air by the pump 14 until the stop of supply of the air.

When the differential pressure between the tensile cuff 74 and the pressing cuff 71 reaches the cracking pressure of the first valve 21, for example, the first valve 21 closes. The air supplied by the pump 14 after the first valve 21 closes is supplied to only the tensile cuff 74.

Note that when the air supplied to the fluid circuit 3G is exhausted, in the fluid circuit 3G, when the pressure of the tensile cuff 74 on the pump 14 side (the primary side) decreases and becomes a predetermined pressure, the second valve 23 and the third valve 26 provided on a bypass path for exhaust opens. Thus, the pressing cuff 71 and the sensing cuff 73 are connected to the atmosphere via the on-off valve 16.

According to the blood pressure measurement device 1G according to the ninth embodiment configured in this manner, the amount of injection of the cuff 71 on the secondary side among the two cuffs 74 and 71 becomes constant by the first fluid control unit 9, and the pressure ratio of the other two cuffs 71 and 73 becomes constant by the second fluid control unit 9G.

Figure 19:
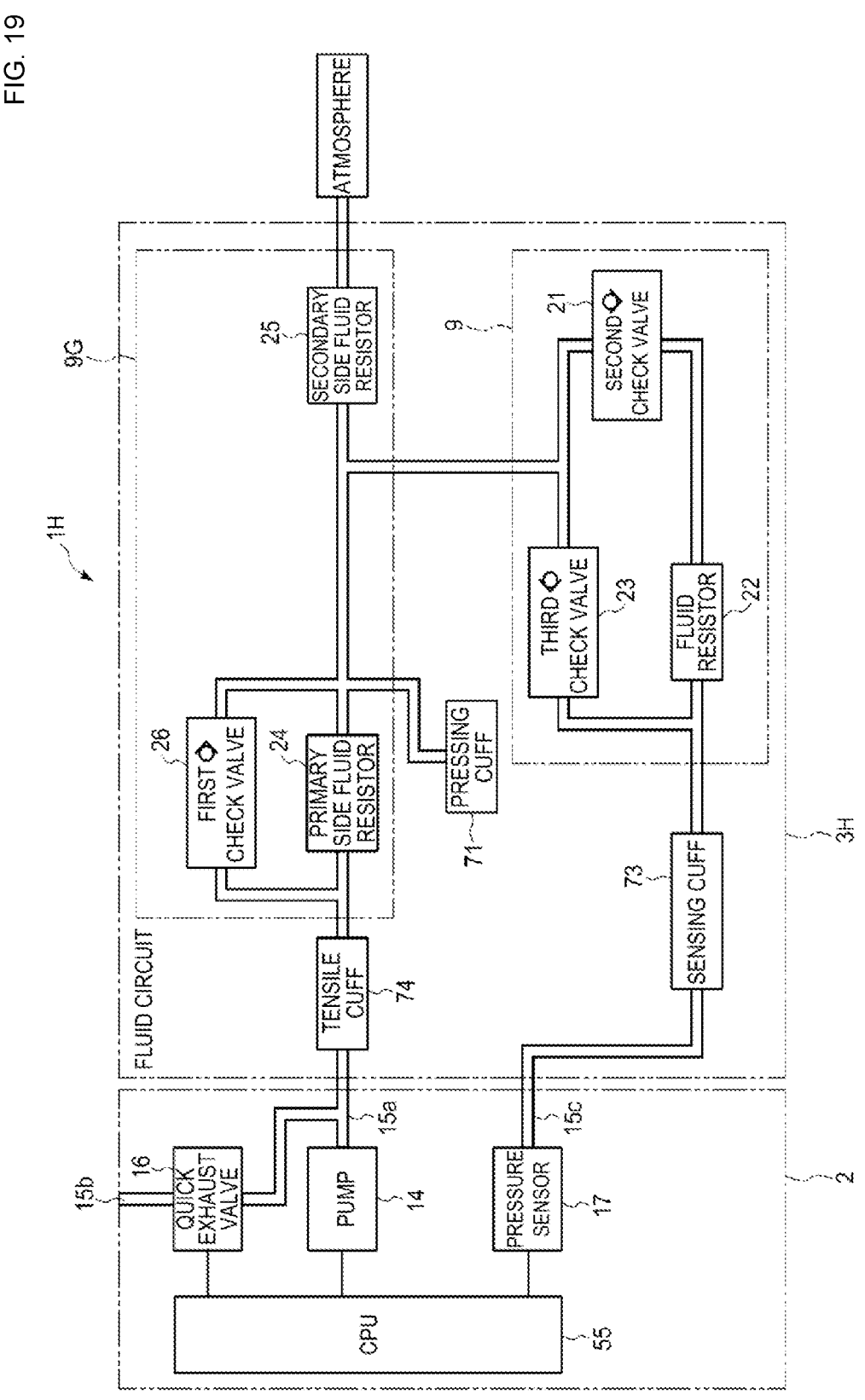

Note that in the present embodiment, as the fluid circuit 3G, the configuration in which the first fluid control unit 9 is provided between the tensile cuff 74 and the pressing cuff 71 and the second fluid control unit 9G is provided between the pressing cuff 71 and the sensing cuff 73 has been described, but the present invention is not limited thereto. For example, as in a fluid circuit 3H of a blood pressure measurement device 1H according to a tenth embodiment illustrated in FIG. 19, the first fluid control unit 9G may be provided between the tensile cuff 74 and the pressing cuff 71 and the second fluid control unit 9 may be provided between the pressing cuff 71 and the sensing cuff 73. The blood pressure measurement device 1H may include the fluid control unit 9A as the second fluid control unit.

Note that the present invention is not limited to the respective embodiments described above. For example, in the cuff structure 6, the plurality of cuffs can be appropriately set, and the cuffs may be other than the pressing cuff, the sensing cuff, the tensile cuff, the winding cuff, or the measurement cuff described above.

Additionally, in the examples described above, the respective components of the fluid circuit 3 are not electrically controlled, and are controlled by the components provided outside the device body 2. However, the configuration is not limited thereto. That is, the fluid circuit 3 may be configured to further include the pump 14, the on-off valve 16, and the pressure sensor 17, in addition to the cuff structure 6, the tube group 7, and the fluid control units 9, 9A, and 9G as the configuration.

Furthermore, in view of miniaturizing the device body 2, the components of the fluid circuit 3 are preferably provided outside the device body 2, but obviously may be housed in the device body 2.

That is, the present invention is not limited to the above-described embodiments, and various modifications can be made in an implementation stage without departing from the gist thereof. Further, each of the embodiments may be carried out as appropriate in a combination as much as possible, and combined effects can be obtained in such case. Further, the inventions at various stages are included in the embodiments, and the various inventions may be extracted in accordance with appropriate combinations in the plurality of disclosed constituent elements.

REFERENCE NUMERALS LIST

1 Blood pressure measurement device
1A Blood pressure measurement device
1B Blood pressure measurement device
1C Blood pressure measurement device
1D Blood pressure measurement device
1E Blood pressure measurement device
1F Blood pressure measurement device
1G Blood pressure measurement device
1H Blood pressure measurement device
2 Device body
2A Device body
3 Fluid circuit
3A Fluid circuit
3F Fluid circuit
3G Fluid circuit
3H Fluid circuit
4 Fixture (belt)
5 Curler 6 Cuff structure
7 Tube group
7a First tube
7b Second tube
7b1 Branch portion
7b2 Tube portion
7b3 Tube portion
7c Third tube
7d Fourth tube
7d1 Joint portion
7d2 Tube portion
7d3 Tube portion
7e Fifth tube
9 Fluid control unit
9A Fluid control unit
9G Fluid control unit
11 Case
12 Display device
13 Operation device
14 Pump
15 Flow path unit
15a Flow path
15b Flow path
15c Flow path
16 On-off valve (first on-off valve)
17 Pressure sensor
18 Power supply unit
19 Communication device
20 Control substrate
21 First valve
21A First valve (switching valve)
22 Fluid resistor
23 Second valve
24 Primary side fluid resistor
25 Secondary side fluid resistor
26 Third valve
31 Outer case
31a Lug
31b Spring rod
32 Windshield
41 Button
43 Touch panel
51 Substrate
54 Storage unit
55 Control unit
55a Measurement processing unit
61 First belt
61a Belt portion
61b Buckle
62 Second belt
71 First cuff
72 Back plate
73 Second cuff
74 Third cuff
81 Air bag
84 Connection portion
91 Air bag
92 Flow path body
93 Connection portion
200 Living body (wrist)
210 Artery

What is claimed is:
1. A fluid circuit, comprising:
a first cuff connected to a secondary side of a pump that supplied a fluid to said secondary side of the pump;
a second cuff connected in series to a secondary side of the first cuff, such that fluid flows sequentially from the pump to the first cuff, then to the first valve, then to a fluid resistor, and then to the second cuff.

2. The fluid circuit according to claim 1, comprising a second valve provided in parallel with the first valve and the fluid resistor, the second valve opening when a 5 pressure of the first cuff is lower than a pressure of the second cuff.

3. A blood pressure measurement device, comprising:
the fluid circuit according to claim 1;
an on-off valve provided between the pump and the first 10 cuff, the on-off valve opening and closing a flow path to an atmosphere;
a pressure sensor connected to the second cuff; and
a control unit that controls the pump and the on-off valve based on a pressure detected by the pressure sensor. 15

4. The blood pressure measurement device according to claim 3, comprising
a device body that houses the pump, the on-off valve, the pressure sensor, and the control unit, wherein
the first valve and the fluid resistor are integrally provided 20 with the first cuff.

5. A blood pressure measurement device, comprising:
the fluid circuit according to claim 2;
an on-off valve provided between the pump and the first cuff, the on-off valve opening and closing a flow path 25 to an atmosphere;
a pressure sensor connected to the second cuff, and
a control unit that controls the pump and the on-off valve based on a pressure detected by the pressure sensor.

* * * * * 30